US012749579B2

(12) United States Patent
Lipton et al.

(10) Patent No.: US 12,749,579 B2
(45) Date of Patent: Sep. 29, 2026

(54) METHODS OF AUTOMATICALLY GENERATING FORMATTED ANNOTATIONS OF DOCTOR-PATIENT CONVERSATIONS

(71) Applicant: Carnegie Mellon University, Pittsburgh, PA (US)

(72) Inventors: Zachary Lipton, Pittsburgh, PA (US); Jeffrey Bigham, Pittsburgh, PA (US); Kundan Krishna, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 310 days.

(21) Appl. No.: 17/736,624

(22) Filed: May 4, 2022

(65) Prior Publication Data

US 2022/0375605 A1 Nov. 24, 2022

Related U.S. Application Data

(60) Provisional application No. 63/183,929, filed on May 4, 2021.

(51) Int. Cl.
*G06F 40/205* (2020.01)
*G06F 40/216* (2020.01)
(Continued)

(52) U.S. Cl.
CPC ........... *G16H 50/20* (2018.01); *G06F 40/205* (2020.01); *G06F 40/216* (2020.01); *G06F 40/30* (2020.01);
(Continued)

(58) Field of Classification Search
CPC ........ G16H 50/20; G16H 10/60; G16H 50/70; G16H 80/00; G06F 40/205
See application file for complete search history.

(56) References Cited

U.S. PATENT DOCUMENTS 11,861,298 B1 * 1/2024 Tackie .................. G06N 20/20
2020/0185102 A1 * 6/2020 Leventhal ............ G06F 40/117
(Continued)

OTHER PUBLICATIONS

Collier; Rich, Filtering Input Data to Refine Machine Learning Jobs, Jun. 5, 2018, elastic (Year: 2018).*
(Continued)

*Primary Examiner* — Shahid Merchant
*Assistant Examiner* — David Choi
(74) *Attorney, Agent, or Firm* — Fish & Richardson P.C.

(57) ABSTRACT

A data processing system accesses a digital resource that includes a plurality of sections and a classifier configured to detect contents representing one or more portions of a communication with increased likelihood of being cited as evidence associated with a particular one of the sections. The data processing system receives a stream of data items representing a communication and generates content for at least one of the sections. The data processing system parses one or more fields in the data items, extracts values from the one or more parsed fields, identifies, by the classifier, that the extracted values are represented in one or more portions of the contents representing the one or more portions of the communication with increased likelihood of being cited as evidence, identifies that the extracted values are associated with a particular section of the digital resource, and generates content for that particular section.

27 Claims, 11 Drawing Sheets

(51) Int. Cl.
*G06F 40/30* (2020.01)
*G16H 10/60* (2018.01)
*G16H 50/20* (2018.01)
*G16H 50/70* (2018.01)
*G16H 80/00* (2018.01)

(52) U.S. Cl.
CPC ............. *G16H 10/60* (2018.01); *G16H 50/70* (2018.01); *G16H 80/00* (2018.01)

(56) References Cited

U.S. PATENT DOCUMENTS

| | | | | |
|---|---|---|---|---|
| 2020/0293712 | A1* | 9/2020 | Potts | G06F 40/169 |
| 2021/0158922 | A1* | 5/2021 | Mahajan | G16H 20/10 |
| 2022/0172725 | A1* | 6/2022 | Khan Khattak | G10L 15/1822 |

OTHER PUBLICATIONS

Hall; Mark A., Feature Selection for Machine Learning: Comparing a Correlation-based Filter Approach to the Wrapper, 1998, University of Waikato, Department of Computer Science (Year: 1998).*

Krishna et al., “Extracting Structured Data from Physician-Patient Conversations by Predicting Noteworthy Utterances,” arXiv, Jul. 14, 2020, 14 pages.

Krishna et al., “Generating SOAP Notes from Doctor-Patient Conversations Using Modular Summarization Techniques,” ArXiv, May 4, 2020, 15 pages.

* cited by examiner

301

Training Dataset

| | | | | |
|---|---|---|---|---|
| Subjective | Noteworthy Utterance 1 | Noteworthy Utterance 2 | ........ | Noteworthy Utterance n |
| Objective | Noteworthy Utterance 1 | Noteworthy Utterance 2 | ........ | Noteworthy Utterance n |
| Assessment | Noteworthy Utterance 1 | Noteworthy Utterance 2 | ........ | Noteworthy Utterance n |
| Plan | Noteworthy Utterance 1 | Noteworthy Utterance 2 | ........ | Noteworthy Utterance n |

FIG. 3

Precision-at-1 at different thresholds of the diagnosis-noteworthy utterance classifier. Average number of noteworthy sentences extracted in parentheses Variation in ROUGE scores averaged over different lengths of input conversation

900

| Cluster of utterances | Subsection | Summary |
|---|---|---|
| **DR** That one thing that we can do to reduce risk with that cholesterol is 100 mg metoprolol.<br>**DR** But I want you on two a day. | Prescriptions and Therapeutics | metoprolol 100 mg twice a day. |
| **DR** Um, you don't smoke?<br>**PT** No.<br>**DR** Okay. | Review of Systems | denies smoking. |
| **DR** Um, the first thing I didn't get was that, um , are you , you 're on digoxin , right?<br>**PT** Um-hum. | Past Medical History | history of heart disease. |
| | Medications | digoxin. |
| | Assessment | the patient is on digoxin. |
| **DR** Uh, and have you had any more chest pain?<br>**PT** I did, yeah, I do. | Review of Systems | confirms chest pain. |
| **DR** Uh, and have you had any more chest pain?<br>**PT** Not really. No. | Review of Systems | denies chest pain. |
| **DR** Um, and then let 's just peek at the x-ray on Thursday.<br>**PT** Okay.<br>**DR** Um, and that's just an x-ray.<br>**DR** It shouldn't be a visit with a copay or anything like that. | Assessment | discussed with the patient that x-ray is not a visit with a copay or anything like that. |
| | Diagnostics and Appointments | x-ray to be done on thursday ( not a visit with a copay or anything like that. |
| **DR** This one, this amlodipine that you are taking it's a good pill for high blood pressure.<br>**PT** Okay<br>**DR** But right now your blood pressure is a bit low.<br>**PT** Um-hum<br>**DR** So I will reduce it to half a pill per day, alright? | Chief Complaint | high blood pressure. |
| | Review of Systems | blood pressure is a bit low. |
| | Past Medical History | high blood pressure. |
| | Prescriptions and Therapeutics | amlodipine half a pill a day. |
| **DR** And nothing like that?<br>**PT** I , and , of course , when you break something , like I fractured my leg , I don't think that whatever that feeling is ever goes away completely. | Chief Complaint | leg swelling. |
| | Past Medical History | leg pain. |
| | Medications | patient is on leg. |
| | Immunizations | patient had a flu shot in the past. |
| | Diagnostics and Appointments | the patient will undergo leg surgery. |

FIG. 9

METHODS OF AUTOMATICALLY GENERATING FORMATTED ANNOTATIONS OF DOCTOR-PATIENT CONVERSATIONS

CLAIM OF PRIORITY

This application claims priority under 35 U.S.C. § 119(e) to U.S. Provisional Application Ser. No. 63/183,929, filed May 4, 2021, the entire contents of which are hereby incorporated by reference.

TECHNICAL FIELD

This specification describes digitization of clinical summaries. More specifically, this specification describes automated production, by use of one or more classifiers or machine learning models, of medical documentation including of conversation transcripts.

BACKGROUND

Medical institutions collect vast amounts of patient Electronic Health Record (EHR) data including but not limited to patient history, family history, past surgeries, medications and more. Such EHR data helps physicians recall past visits, assess patient conditions over time, and learn crucial information (for e.g., drug allergies) in emergency scenarios. However, EHR data is tedious and time consuming for physicians to produce. For example, only one-third of a physician's time is spent with their patients, while two-thirds of the physician's time is dedicated to documenting those patient encounters, i.e., for every hour of visiting patients, physicians spend approximately 45 minutes for EHR documentation. Physicians often need to complete documentation outside of work hours which contributes to physician burnout. Physicians spend much of the EHR documentation time recalling and manually entering information discussed with the patient (for e.g., reported symptoms). This information is often documented in the form of a SOAP (i.e., "Subjective, Objective, Assessment, and Plan") note.

SUMMARY

This specification describes systems and methods for automatic generation, by a data processing system, of formatted annotations of conversations, such as conversations between patients and doctors. The annotations are formatted to satisfy requirements of SOAP documentation that is present in EHR. The annotations describe the conversation and include specific information summarizing the conversation. The data processing system is configured to receive a dataset including conversation transcripts, post-visit summaries, corresponding supporting evidence (in the transcript), and structured labels. The data processing system is configured to recognize relevant diagnoses and abnormalities in the review of organ systems (RoS).

The data processing system and processes described in this specification are configured to provide one or more of the following advantages. The data processing system is configured to overcome a methodological challenge of extracting data of interest from lengthy conversations (e.g., about 1500 words). Generally, this input is too large for use as input to deep-learning models. To overcome this technical obstacle, the data processing system extracts portions of the conversations that are likely to be cited as evidence supporting a summary sentence. This is performed by first filtering transcript data for (predicted) phrases or collections of sentences that are of increased significance relative to the remainder of the transcript. These phrases or collections of sentences are called noteworthy utterances. The filtering-based approach to pre-select noteworthy utterances before feeding these data into a classification model significantly improves the performance of the automated models, increasing micro-averaged F1 scores by 10 points for diagnosis prediction and 5 points for RoS abnormality prediction.

Generally, for the machine learning models described in this specification (e.g., CBERT), pre-filtering reduces a processing time for classifying the entire length of a conversation substantially, as the CBERT machine learning model has a quadratic time $O(n^2)$ runtime. Therefore, a reduction of conversation length reduces runtime substantially based on the quadratic relationship. Additionally, the if logistic regression is used, the processing time is linear $O(n)$ with respect to conversation length. The processing runtime for step (iii) is reduced significantly because the machine learning model (e.g., CBERT) evaluates far less data after pre-filtering occurs. If pre-filtering technique is non-linear (e.g. UMLS, which includes keyword extraction) reduction in processing time is relatively smaller in comparison to the logical regression approach. In an example, if the pre-filtering mechanism is based on logistic regression, and the main bottleneck is a CBERT machine learning model, the data processing system 110 can improve processing time about $K^2$ times faster, where K is the factor by which the conversation is made shorter. For example, when pre-filtering reduces conversation size by 4 times, the overall processing will be 16 times faster. In this way, the data processing system improves predictive performance for recognizing both diagnoses and RoS abnormalities.

Additionally, manual generation of SOAP notes is a tedious and time consuming process and can take up a sizable porting of the physician's workday. Automated generation of a SOAP note from every patient visit can greatly improve the time and efficiency of physicians. The techniques described herein provide machine learning approaches that leverage transcripts of conversations that take place between physicians and patients during a visit, to automatically generate structured SOAP notes. Techniques for automated generation of SOAP notes provided herein can improve the efficiency of EHR documentation.

One aspect of the present disclosure is directed to a computer-implemented method for generating content. The method includes accessing a digital resource that includes a plurality of sections. The method includes accessing, from a hardware storage device, a classifier configured to detect contents representing one or more portions of a communication with increased likelihood of being cited as evidence associated with a particular one of the sections, relative to a likelihood of one or more portions of another communication being cited as the evidence. The method includes receiving, from one or more data sources, a stream of data items representing a communication, with each data item being structured with fields and corresponding values. The method includes generating content for at least one of the sections by: parsing, by the data processing system, one or more fields in one or more of the received data items; extracting, by the data processing system, values from the one or more parsed fields; identifying, by the classifier, that the extracted values are represented in one or more portions of the contents representing the one or more portions of the communication with increased likelihood of being cited as evidence; based on the one or more portions of the contents that represent the extracted values, identifying that the extracted values are associated with a particular section of the digital resource; and based on the extracted values and a proximity of the extracted values to each other in the one or more of the received data items, generating content for that particular section.

In some implementations, the content generated for the particular section is generated in response to identifying, by the classifier, a diagnosis or symptom associated with the extracted values.

In some implementations, the process includes receiving metadata values associated with the extracted values, the metadata values representing one or more of a speaker identity or a temporal position in the stream of data items representing the communication. The process includes generating content for the particular section based on the metadata values associated with the extracted values.

In some implementations, sections include a subjective section include data representing at least one of patient behavior of a patient, patient complaint, symptoms, progress from last encounter, problem, medical issues impacting or influencing patient's day-to-day routine, family history, medical history, and a social history communicated in the communication. In some implementations, the sections include an objective section including data representing quantifiable data of the communicated in the communication. In some implementations, the sections include an assessment section including data representing at least one of a physician diagnoses. In some implementations, the sections include a plan section representing plans for future care of the patient.

In some implementations, the process includes training data representing labeled portions of communications with increased likelihood of being cited as evidence associated with a given section. The process includes training the classifier using the training data. The process includes identifying, by the classifier, based on the training, that the extracted values are represented in one or more portions of the contents representing the one or more portions of the communication with increased likelihood of being cited as evidence.

In some implementations, the process includes obtaining audio data representing the communication. In some implementations, the process includes generating, using natural language processing (NLP), the stream of data items representing the communication, the stream of data items comprises a transcript of the communication.

In some implementations, the process includes merging two or more extracted values into a merged value representing the two or more values. In some implementations, generating content for the particular section is based on the merged value.

In some implementations, the process includes pre-filtering the extracted values from the one or more parsed fields for sending to the classifier. In some implementations, the pre-filtering includes determining that the extracted values from the one or more parsed fields match values previously classified as representing one or more portions of a given communication with increased likelihood of being cited as evidence.

In some implementations, the process includes pre-filtering the extracted values from the one or more parsed fields for sending to the classifier. The pre-filtering includes determining that the extracted values from the one or more parsed fields are associated with a particular diagnosis or a particular symptom defined in a medical-entity-matching baseline.

In some implementations, the process includes generating a structured entry for a data store, the structured entry including the generated content for that particular section. The process includes sending the structured entry to the data store for storage of the structured entry.

The details of one or more embodiments of these systems and methods are set forth in the accompanying drawings and the description to be presented. Other features, objects, and advantages of these systems and methods will be apparent from the description and drawings, and from the claims.

BRIEF DESCRIPTION OF THE DRAWINGS

For simplicity and clarity of illustration, elements shown in the figures have not necessarily been drawn to scale. For example, the dimensions of some of the elements may be exaggerated relative to other elements for clarity of presentation.

FIG. 3 is an exemplary table, consistent with disclosed embodiments.

FIG. 9 is an exemplary graphical representation, consistent with disclosed embodiments.

DETAILED DESCRIPTION

Figure 1:
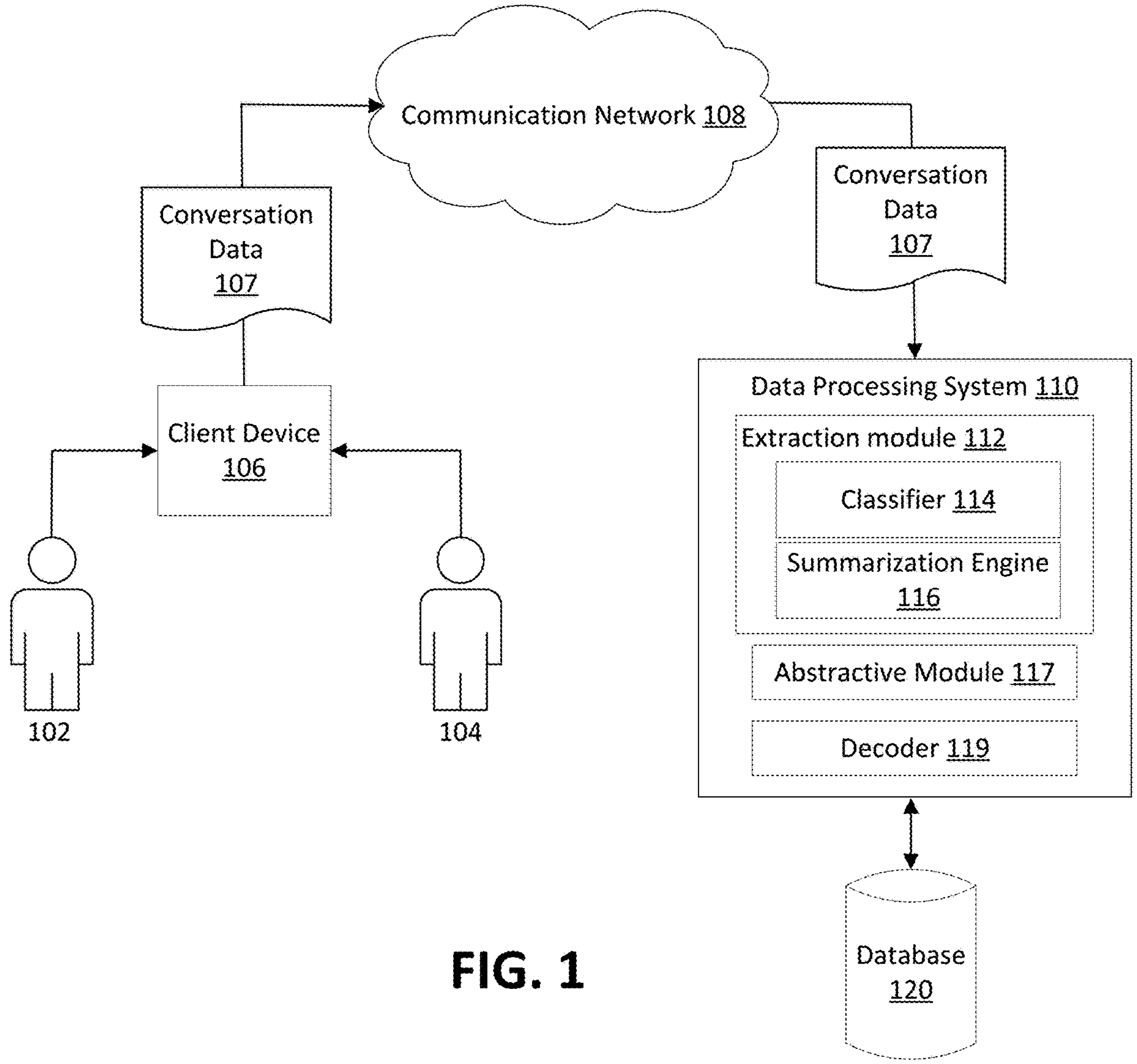
FIG. 1 is a schematic block diagram of an exemplary system, consistent with disclosed embodiments.

FIG. 1 is a block diagram of an exemplary system 100, for performing one or more operations consistent with disclosed embodiments. FIG. 1 shows system 100 for automatically denigrating a SOAP note from a session between physician 102 and patient 104. As illustrated in FIG. 1, system 100 may include a variety of systems, each of which may be connected to one another via one or more communication networks. Components of system 100 may include one or more computing devices (e.g., mobile phone(s), computer(s), server(s), etc.), memory storing data and/or software instructions (e.g., database(s), hardware storage device(s), memory device(s), etc.), and other known computing components. In some embodiments, the one or more computing devices may be configured to execute software instructions stored on one or more memory devices to perform one or more operations consistent with the disclosed embodiments.

The data processing system 110 is configured for automatic generation of formatted annotations for Electronic Health Records (EHR) from patient-physician conversations. The data processing system 110 is configured for prediction tasks using the physician-patient conversation as input. A first prediction task includes relevant diagnosis prediction. A second prediction task includes organ system abnormality prediction. These prediction tasks are examples presented in the present disclosure and are representative of other prediction tasks that are configurable using the methods and systems described herein.

In the first prediction task, the data processing system 110 is configured to extract a set of diagnoses mentioned in the conversations that are relevant to a chief complaint of a patient. This chief complaint describes a primary purpose of the visit. The data processing system 110 configures the first prediction task to omit irrelevant diagnosis. For example, a patient's diagnosis of hypercholesteremia (high cholesterol) may be relevant if his visit is for hypertension but not relevant if the visit is for common cold.

For the second task, the data processing system 110 is configured to recognize organ systems for which a patient reported an abnormal symptom during a review. For example, a patient whose chief complaint is diabetes might report fatigue (a symptom) indicating a musculoskeletal (a related system) abnormality. Taken together, the diagnoses and symptomatic organ prediction systems of the data processing system 110 provide a high-level overview of patient status to aid physicians in post-visit EHR documentation.

The data processing system 110 is configured to generate these predictions (and other similar predictions) based on machine learning processes described herein. The machine learning processes include multi-label classification. The data processing system 110 evaluates task performance for a medical-entity-based string-matching baseline using one or more of traditional learning approaches, such as logistic regression. In some implementations, the data processing system 110 uses complex neural approaches for machine learning, such as Bidirectional Encoder Representations from Transformers (BERT) or other similar natural language processing techniques.

The data processing system 110 is configured to generate structured data representing formatted annotations conforming to a particular standard, known as SOAP (Subjective, Objective, Assessment, and Plan) records or SOAP notes. SOAP notes include formatted annotations that document information including detailed clinical summaries for each patient, collected directly from patients during their visit. The SOAP record is a widely used format for taking medical notes or summaries. The summaries collected in the SOAP records are digitized and stored in an EHR. SOAP are the four major sections of the problem-oriented medical note. SOAP records include semi-structured written accounts or summaries of patient visits, including four sections. Subjective information (S) reported by the patient includes one or more of patient behavior, patient complaint, symptoms, progress from last encounter, problem, medical issues impacting or influencing patient's day-to-day routine, family history, medical history, social history, and so forth. Objective observations (O) include quantifiable and measurable data in the SOAP record. Objective observations include lab results, x-rays, ultrasounds, other relevant diagnostic information, including electrocardiograms, physician's observations from physical examinations, and so forth. Assessments data (A) of the SOAP note include assessments data generated by the doctor. Assessment data include physician diagnoses made by interpreting the information given by the patient during the visit, observation of previous and new symptoms, clinical stability, and any synthesis of the Subjective and Objective sections made by the physician. Plan data (P) include data indicative of plans for future care. Plan data include indication of further investigation of the problem, diagnostic tests, investigated medications, treatments, follow-up protocol, and so forth. Each section of SOAP is further divided into subsections giving it a finer substructure. For example, the subjective section S includes multiple subsections such as a chief complaint section (e.g., a primary reason for a patient's visit), an allergies section, a past medical history section, and so forth. Generally, a particular visit may not have information relevant to each subsection. As a result, some of the subsections may be empty. The fraction of times a subsection is populated varies widely. For example, an allergies section is generally a sparsest populated overall (present in about 4% of notes), while a chief complaint section is generally the most frequently observed (generally present in every record).

The automated generation of a SOAP note from a live physician-patient session increases the time a physician can spend with patients. Physicians and patients capture audio from their sessions, which can be used to generate automated SOAP notes. The data processing system 110 generates automated SOAP notes using the audio recording of patient-physician sessions, whether the sessions are held in-person or via tele-conferencing or video conferencing. Prior to extraction of noteworthy utterances, the data processing system 110 generates transcripts using the recorded sessions between the physician and the patient. The data processing system 110 produces an evaluation of complete processing pipelines to use the generated transcripts for training machine learning models to generate SOAP notes. In some embodiments, a unique dataset of patient visit records, including of transcripts, paired SOAP notes, and annotations marking noteworthy utterances that support each summary sentence can be generated. A historical dataset of patient visit records, including of transcripts, paired SOAP notes, and annotations marking noteworthy utterances that support each summary sentence can be stored in a database. The historical dataset is generated using thousands of previous physician-patient encounters. In some embodiments, the captured sessions can be stored as an audio recording and transcribed using automatic speech recognition (ASR) to extract and summarize clinically relevant information with natural language understanding (NLU).

Noteworthy utterances include relevant keywords with respect to one or more of the four (S, O, A, P) sections. The data processing system 110 automatically identifies and classifies transcript data and associated metadata in a physician-patient session based on that data's relevance to different parts of the SOAP note. The data processing system 110 distinguishes whether a particular utterance was stated by the patient or the physician.

The data processing system 110 processes conversation data 107 collected during the physician-patient session to decompose the problem into extractive and abstractive subtasks. The data processing system 110 extracts the noteworthy utterances using multi-label classification. The data processing system 110 assigns the extracted noteworthy utterances to summary section(s). The data processing system 110 clusters the noteworthy utterances on a per-section basis. The data processing system 110 generates summary sentences by conditioning on the corresponding cluster and the subsection of the SOAP sentence to be generated. The data processing system 110 uses a neural network or other trained machine learning model to analyze the physician-patient sessions and update the model using feedback data from the physician provided after one or more encounters.

A database communicatively coupled to the data processing system 110 stores historical data including of thousands of recorded clinical conversations with associated SOAP notes created by a work force trained in the official style of SOAP note documentation. The historical data includes automatic speech recognition (ASR) transcriptions of these conversations and machine learning optimized SOAP notes based on the human generated transcripts. The data processing system 110 uses the historical data to iteratively train the machine learning model. While discussed in the context of a neural network, it is understood that various and multiple machine learning networks and methodologies can be used to train a model for use in automatically generating a SOAP note.

Generally, SOAP notes generated are relatively long (about 320 words on average). The data processing system 110 is configured to overcome dual challenges of (i) generating coherent summaries much longer than those demanded by traditional benchmark tasks; and (ii) handling specialized medical terminology. The data processing system 110 overcomes these technical challenges as subsequently described. The data processing system 110 generates useful structure in the form of additional annotations that (i) segment each note into 15 subsections (not every subsection features in every note); and (ii) identify, for each sentence in the note, a set of corresponding supporting utterances in the conversation. The summarization algorithms discussed herein use the annotations to achieve better performance on the task. For example, the ROUGE metric shows how performance is improved, as subsequently described in relation to Table 8. While ROUGE-1, ROUGE-2, and ROUGE-3 results are shown in Table 8, the performance increase is illustrated by discussion of ROUGE 1, here. Steps (i) and (ii) correspond to the method labelled SectionwiseSummaryGeneration (BERT-LSTM) which has a ROUGE-1 score of 0.5222. The baseline method, called FullConversationToFullSummary, has ROUGE-1 of 0.4894. This shows a statistically significant improvement to classification. To further improve the result, the process called SentencewiseSummaryGeneration (BERT-LSTM) can be performed by the data processing system 110. This process has a ROUGE-1 score 0.5648, showing additional improvement. As subsequently described, the data processing system 110 achieves this improvement by an additional step (iii) which creates clusters of supporting utterances which are related to each other and summarizes each cluster separately to produce a one-sentence summary for each cluster.

The data processing system 110 includes an extraction module that selects noteworthy utterances from the physician-patient conversation for different sections and clusters related extracted utterances to generate a one-line summary for each of those clusters while conditioning on the section of the SOAP note being generated. Such a modular approach to SOAP note generation reduces the burden on the abstractive component. The modular approach achieves better ROUGE scores compared to an end-to-end approach of generating full SOAP note from full summary. The modular approach generates a more interpretable model in which every output sentence comes with the noteworthy utterances that were used for its creation. The data processing system 110 is configured to generate relatively long (e.g., more than 300 words) SOAP notes automatically and lighten the burden on doctors.

The data processing system 110 is configured to use one of several approaches described to generate the SOAP notes. The data processing system 110 allocates work among subtasks. In a first scenario, an extraction module 112 does nothing, placing a full burden of summarization on an end-to-end abstractive module 117. In a second scenario, the extraction module 112 extracts all noteworthy utterances, and a decoder is trained only on these utterances. In a third scenario the extraction module 112 extracts per-section utterances and the decoder 119 generates each subsection, conditioned only on those utterances predicted to support sentences in that subsection. In a fourth scenario, the extraction module 112 extracts per-subsection noteworthy utterances and additionally clusters them. In this scenario, the decoder 119 produces a single sentence at a time, each conditioned upon a single cluster of supporting sentences. The data includes annotations for extraction, allowing to directly train the extraction modules 112 and to evaluate the decoding modules 119 in an oracle setting (assuming perfect extraction).

Generally, the extraction module 112 centric approach (scenario two) is performed to result in the following benefits. Given oracle per-section noteworthy utterances, a proximity-based clustering heuristic performs nearly as well as the ground-truth groupings by most metrics, even though the ground truth groupings are not always localized. In addition to achieving the highest ROUGE scores, the extraction-centric scenario localizes the precise sentences upon which each SOAP note sentence depends, enabling physicians to (i) verify the correctness of each sentence and (ii) to improve the draft by highlighting sentences, in contrast with revising the text directly. The extraction module 112 centric approach includes a hierarchical model in which a pre-trained BERT model encodes each sentence. Subsequently, a bidirectional LSTM classifies each utterance as noteworthy or not for each subsection (multi-label classification). In the abstractive phase, this approach builds on the pointer-generator model, additionally conditioning on the identity of the subsection to be generated.

The various embodiments disclosed herein can be summarized to perform the following: The first pipeline for drafting entire SOAP notes from doctor-patient conversations. An exploration of methods of modularizing the task into extractive and an abstractive components, demonstrating the benefits of shifting maximal burden to extraction. A rigorous quantitative evaluation of several strong approaches to each subtask. A qualitative evaluation of the produced SOAP notes, characterizing the errors that both models make, and the impact of per-section conditioning.

In some embodiments, system 100 includes one or more client devices 106, one or more data processing system systems 110, one or more databases 120, and a communication network 108. The components and arrangement of the components included in system 100 may vary. Thus, system 100 may include other components that perform or assist in the performance of one or more processes consistent with the disclosed embodiments.

Components of system 100 may be configured to generate automated SOAP notes using a dataset of physician-patient conversations. Client device 106 may include, but are not limited to, computers, personal computers, portable computing devices including audio recorder, two-way audio and/or video conferencing device, hand-held computers, personal digital assistants, mobile phones, and cellular telephones. Client device 106 may be equipped with hardware and software configured to capture, record, reproduce, transmit, and receive audio and/or video data to or from another computing device. Client device 106 may be equipped to capture an audio recording or conversation data of a patient-physician session, providing high-quality audio capture of the session. Client device 106 may be equipped to use ASR and natural language understanding (NLU) to generate transcripts of the conversation data 107. Client device 106 may further include a server or access to cloud infrastructure via network 108 to provide clinical documentation tools and/or access to the electronic medical record ("EMR") within a number of hospitals, hospital networks, other care facilities, or any other type of medical information system. The software may have access to identification of patient 104 being examined as well as access to their EMR. The software may also have access to, for example, notes from any medical staff that may have been entered in real time or that may have been previously entered. Client device 106 may be equipped to transmit the conversation data 107 to data processing system 110 via communication network 108.

Data processing system 110 and client device 106 may be configured to communicate with each other over communication network 108. Communication network 108, herein referred to as network 108 may include, but is not limited to, wired networks, wireless networks, and combined wired and wireless networks. For example, network 108 may include any type of network (including infrastructure) that provides communications, exchanges information, and/or facilitates the exchange of information, such as the Internet, a private data network, a virtual private network using a public network, a LAN or WAN network, a Wi-Fi™ network, and/or other suitable connections that may enable information exchange among various components of system 100. Network 106 may also include a public switched telephone network ("PSTN") and/or a wireless cellular network. Network 108 may be a secured network or unsecured network. In some embodiments, one or more components of system 100 may communicate directly through a dedicated communication link(s).

In some embodiments, data processing system 110 can be communicatively coupled to database 120. Data processing system 110 can be configured to generate automated SOAP notes using conversation data 107 obtained from client device 106. In some embodiments, data processing system 110 receives conversation data 107 from client device 106, transcribes the conversation data 107, extracts clinically relevant information, and makes clinical inferences to assist both physicians and patients with organizing medical information and generating SOAP notes. Data processing system 110 may be equipped to use ASR and natural language understanding (NLU) to transcribe the conversation data 107. Every communication between physician 102 and patient 104 can be transcribed by data processing system 110. Transcription may begin immediately upon commencement of the patient-physician session. Data processing system 110 includes extraction module 112, which includes a classifier 114 and a summarization engine 112. Extraction module 112 is configured to leverage the transcribed physician-patient conversations to automatically extract structured data.

Database 120 of system 100, may be communicatively coupled to data processing system 110 and client device 106 via network 108. Database 120 may include one or more memory devices that store information and are accessed and/or managed by one or more components of system 100. By way of example, database 106 may include Oracle™ databases, Sybase™ databases, or other relational databases or non-relational databases, such as Hadoop sequence files, HBase, or Cassandra. Database 120 may include computing components (e.g., database management system, database server, etc.) configured to receive and process requests for data stored in memory devices of database 120 and to provide data from database 120.

Generating transcribed data of conversations between physician 102 and patient 104 to extract structured information assists physicians with post-visit documentation in electronic health records, lightening the clerical burden. The data processing system 110 generates a dataset including of conversation transcripts, post-visit summaries, corresponding supporting evidence (in the transcript), and structured labels. The data processing system 110 is configured to recognize relevant diagnoses and abnormalities in the review of organ systems (RoS).

The data processing system 110 maps or links each noteworthy utterance to a piece of evidence. The data processing system 110 obtains evidence based on a systematic review of medical literature (such as medical journals, research papers, books, etc.) to evaluate the best indication of a specific clinical condition.

As previously described, the data processing system 110 formulates the tasks as multi-label classification problems and evaluates task performance for a medical-entity-based string-matching baseline, traditional learning approaches, and neural approaches. As previously discussed, the data processing system 110 uses a filtering-based approach to pre-select noteworthy utterances before feeding them into classifier 114.

Different ways of extracting noteworthy utterances are used by data processing system 110. In an example, a medical entity tagger (e.g., a module or system configured to receive user interaction) labels the utterances. The data processing system 110 trains a model to predict such utterances using annotations present in the dataset. Generally, the data processing system 110 uses sentences that are specifically noteworthy with respect to medical diagnoses for diagnosis prediction tasks. For the RoS abnormality prediction task, the best performance is achieved when using sentences extracted by a medical entity tagger along with sentences predicted to be noteworthy with respect to review of systems.

Figure 2A:
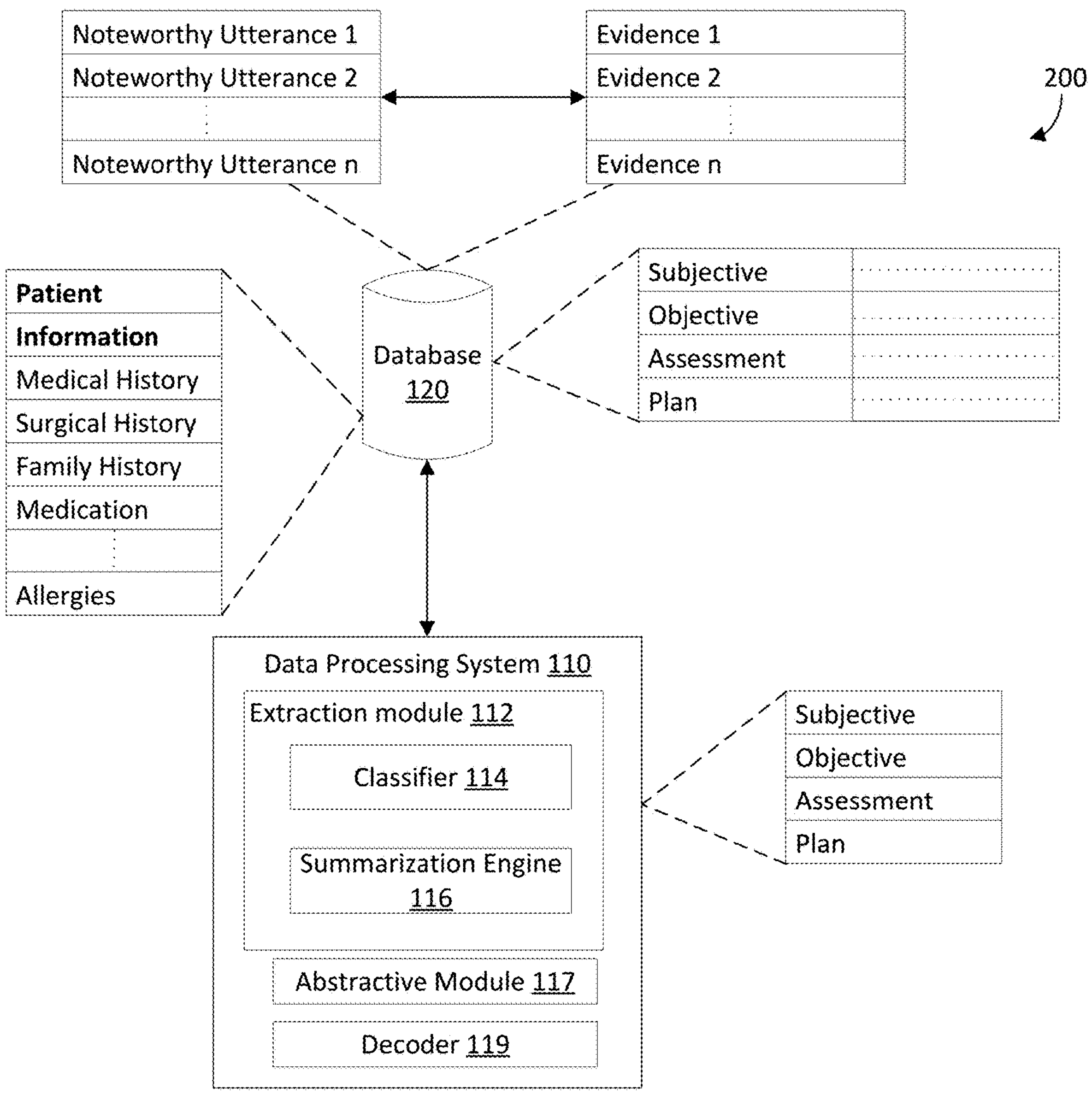
FIG. 2A is a block diagram of an exemplary data processing system, consistent with disclosed embodiments.

The historical dataset of patient visit records, including transcripts, paired SOAP notes, and annotations marking noteworthy utterances that support each summary sentence, are stored in a database 120. The historical dataset is generated using thousands of previous physician-patient encounters. FIG. 2A is a block diagram of an exemplary data processing system 110, consistent with disclosed embodiments. FIG. 2A shows elements 200 included in the database 120, which includes historical dataset of patient visit records. Generally, database 120 is a hardware storage device that stores data records. Each data record has fields with values. For example, a patient data record stored in database 120 may include the name of a field representing patient information and value of the field represents the value of the patient information, for example, medical history, surgical history, allergies, etc. Database 120 may also store noteworthy utterances and evidences leading to the noteworthy utterances. Mapping of each noteworthy utterance to an evidence may be done by integrating the experience of physician 102 and the best available scientific information. Mapping of noteworthy utterance to evidence may make decision making more structured and objective. Mapped noteworthy utterance and evidence may be stored in database 120 as shown in FIG. 2B.

Figure 2B:
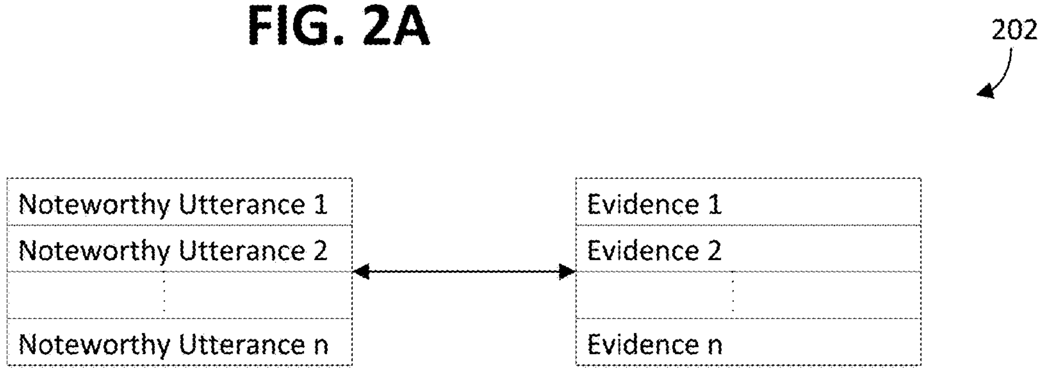
FIG. 2B is an exemplary table, consistent with disclosed embodiments.

The data processing system 110 is configured to map a specific noteworthy utterance to an evidence and store the mapping within the database 120, as shown in FIG. 2B. The mapping 202 or linking of a noteworthy utterance to an evidence may also be performed manually by a medical professional (for e.g., a physician, a nurse practitioner or any other medical staff member) to be uploaded and stored in database 120 as shown in FIG. 2B. The system described herein parses the data records to identify noteworthy utterances corresponding to an evidence to automatically generate a summary of the patient-physician visit i.e., automatically generate a SOAP note.

The data processing system 110 is configured to train a prediction model to detect noteworthy utterances from transcribed data. The prediction model may also be trained to detect if a noteworthy utterance may be classified into a relevant section of the SOAP note. For example, a noteworthy utterance may be classified as being a part of Subjective dataset, Objective dataset, Assessment dataset or Plan dataset.

Upon detecting that a noteworthy utterance can be mapped to either one of the four sections of the SOAP note, the data processing system 110 generates a training dataset. As shown in FIG. 3, a training dataset 301 includes noteworthy utterances mapped to one of the four sections of the SOAP note. The data processing system 110 generates the training dataset 301 using historical SOAP notes generated by using EHR data, including data collected from previous physician-patient sessions. The data processing system 110 generates the training dataset 301 using up to or more than thousands of real-life patient-physician visits over a period of time. The data processing system 110 couples the transcribed conversations with corresponding structured text summaries and summary annotations. The structured text summaries (e.g., SOAP notes typically written by a physician to summarize a patient visit) and their annotations are constructed by expert clinical annotators who received task-specific training. For each visit, a human generated transcript of the conversation and human drafted SOAP note are used to input noteworthy utterances to the data processing system 110 and classify them as Subjective, Objective, Assessment or Plan.

Figure 4:
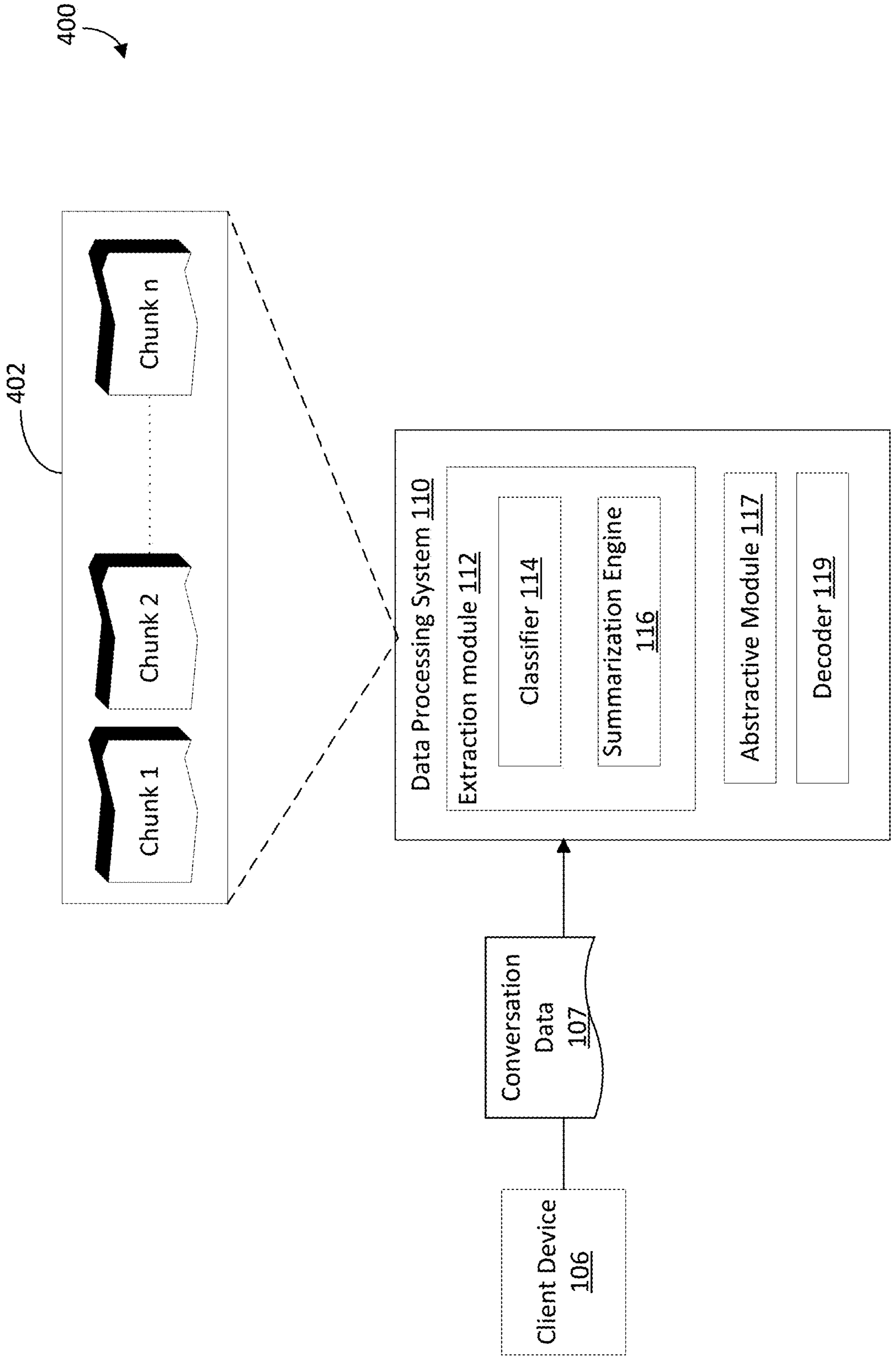
FIG. 4 is an exemplary process, consistent with disclosed embodiments.
Figure 5:
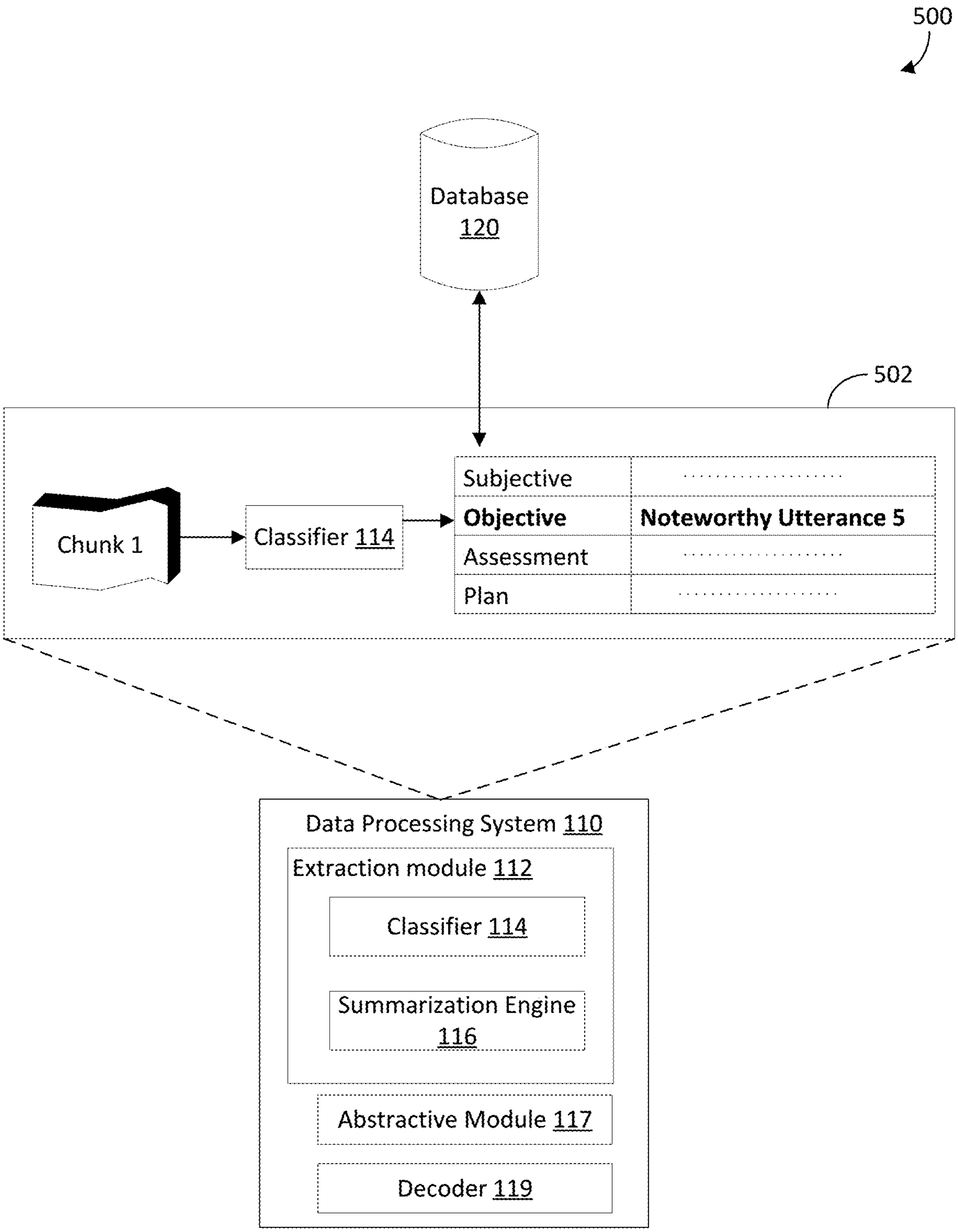
FIG. 5 is an exemplary process, consistent with disclosed embodiments.

FIG. 4 shows a workflow 400 for processing conversations by the data processing system 110. In some embodiments, client device 106 may record a physician-patient session amounting to for example, 15 minutes of conversation. As shown in FIG. 4, conversation data 107 representing 15 minutes of conversation are transmitted to data processing system 110. The data processing system 110 transcribes the conversation data 107 and divides the conversation data into plurality of data chunks (e.g., chunk 1 . . . chunk n) to detect noteworthy utterances from each of the data chunks. The extraction module 112 of the data processing system 110 includes a classifier 114 and a summarization engine 116. As depicted in the workflow 500 shown in FIG. 5, each of the data chunks is fed to the classifier 114 in process 502. The classifier 114 uses training dataset 301 to classify data from every chunk and identify a noteworthy utterance and map it to one of the four sections of the SOAP note. For example, in some embodiments, a conversation between a physician and a patient may be transcribed by data processing system 110 as follows in the given example data.

Doctor (DR): So are you taking the Montelukast regularly?

Patient (PT): Yeah, one everyday like you said.

DR: Good. And is it helping? Do you have chest pains anymore?

PT: No. No chest pains.

DR: That's good.

PT: Although I do still have some cough.

DR: I see. And do you get, like, mucous with it or is it dry?

PT: Umm no it's usually dry. No mucous.

The data processing system 110 generates chunks of data from the above conversation. For example, a first data chunk includes "(DR) Good. And is it helping? Do you have chest pains anymore? (PT) No. No chest pains although I do still have some cough." When the classifier 114 receives the first data chunk (chunk 1), the classifier 114 identifies a noteworthy utterance that the patient is denying having chest pains, but confirming having dry cough. The classifier 114 accesses the training dataset 301 from database 106 and identify if the identified noteworthy utterance may be mapped to any of the four sections of the SOAP note. From the training dataset 301, classifier 114 identifies that the detected noteworthy utterance may be mapped to the "Subjective" section of the SOAP note.

Continuing with this example, chunk 2 may include: "(PT) No. No chest pains although I do still have some cough. (DR) I see. And do you get, like, mucous with it or is it dry? (PT) Umm no it's usually dry. No mucous." When classifier 114 receives data chunk 2, the classifier 114 may identify two noteworthy utterances that the patient is having "dry cough" but "no mucus". The classifier 114 may access the training dataset 301 from database 106 and identify whether the identified noteworthy utterance "dry cough" may be mapped to any of the four sections of the SOAP note. From the training dataset 301, the classifier 114 identifies that the detected noteworthy utterance is mapped to the "Subjective" section of the SOAP note. From the training dataset 301, the classifier 114 further identifies, in this example, that noteworthy utterance "no mucus" is mapped to "Assessment" section of the SOAP note.

Continuing with this example, data chunk 3 may include "(DR) So are you taking Montelukast regularly? (PT) Yes, one every day." When classifier 114 receives data chunk 3, the classifier identifies that "Montelukast" is a medication used for treating chest pain by accessing the training dataset 301 from database 106. The classifier 114 classifies data chunk 3 as including a noteworthy utterance related to an ongoing medication and map it to the "Subjective" section of the SOAP note.

The summarization engine 116 may use the data from classifier 114 to summarize the conversation and generate an automated SOAP note. Continuing the above example, the summarization engine 116 generates the following exemplary SOAP note.

Subjective

Chief Complaint—Post viral respiratory allergy

Review of systems—Denies chest pain. Confirms dry cough.

No fever

Medications—Montelukast. Fluticasone

Objective

Lab results—

Assessment

Assessment—Patient feeling better after taking inhaler. Still has some cough but no chest pain.

Plan

Diagnostics and Appointments—Follow up in 1 week to assess condition and decide when to stop using the inhaler.

Figure 6A:
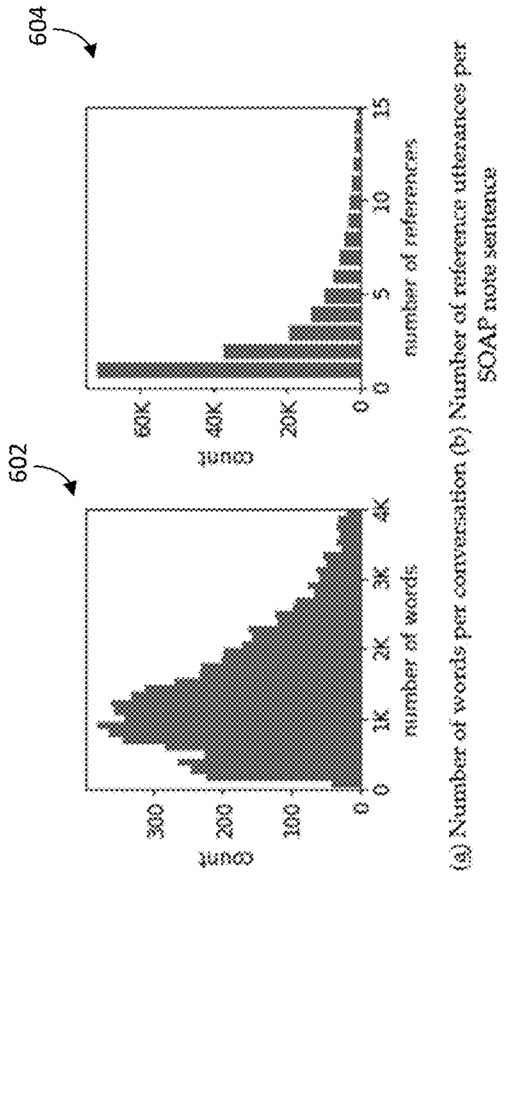
FIGS. 6A and 6B are exemplary graphical representations, consistent with disclosed embodiments.

The dataset used to generate training dataset 301 includes of transcripts from real-life patient-physician visits. For each visit, a human-generated transcript of the conversation is stored in database 106. The utterances are segmented by speaker. Each utterance can be associated with a timestamp. In a given example, an average conversation may last 9 minutes and 26 seconds and may include of about 1500 spoken words, as shown in graphs 602 and 604 of FIG. 6A. FIG. 6A shows graphs 602, 604 representing a distribution of number of words in physician-patient conversations and the number of evidence utterances referred by a sentence of a SOAP note. Along with the conversation, trained, professional annotators generate a human-drafted SOAP note. In a particular example, a dataset used to generate the training dataset 301 represented 6862 visits including 2732 cardiologist visits, 2731 visits for family medicine, 989 interventional cardiologist visits, and 410 internist visits. In some implementations, the dataset may be divided into train, validation and test splits of size 6270, 500 and 592 respectively.

In some embodiments, annotated SOAP notes include (up to) 15 subsections, each of which may include multiple sentences. The subsections vary in length. Table 1 (produced below) shows subsections for every section of the SOAP note, mean length of every subsection and total mean length of every section. The data shown in Table 1 includes the dataset used to generate training dataset 301, which includes transcripts from real-life patient-physician visits as previously described. In a particular example, the "Allergies" subsections were most often empty, while the "Assessment" subsection included 5.16 sentences on average. The average SOAP note included 27.47 sentences. The different subsections differ in the style of writing. The Medications subsection usually includes bulleted names of medicines and their dosages, while the Assessment subsection typically includes full English sentences.

TABLE 1

Different sections and subsections in a SOAP note in our dataset with mean lengths measured in terms of number of sentences

| Section | Subsection | Mean length | Total mean length |
|---|---|---|---|
| Subjective | Family Medical History | 0.23 | |
| | Past Surgical History | 0.58 | |
| | Review of Systems | 3.65 | |
| | Chief Complaint | 2.17 | |
| | Miscellaneous | 2.81 | |
| | Allergies | 0.06 | |
| | Past Medical History | 2.93 | |
| | Social History | 0.27 | |
| | Medications | 3.74 | 16.44 |
| Objective | Immunizations | 0.11 | |
| | Laboratory and Imaging Results | 2.27 | 2.38 |
| Assessment | Assessment | 5.16 | 5.16 |
| Plan | Diagnostics and Appointments | 1.65 | |
| | Prescriptions and Therapeutics | 1.75 | 3.40 |
| Other | Healthcare Complaints | 0.09 | 0.09 |

The data processing system 110 annotates sentences in the SOAP note with utterances from the conversation which are supporting evidence for that SOAP note sentence. A sentence in the SOAP note can have one or more supporting utterances, and on an average there may be 3.85 supporting utterances per SOAP note sentence. However, the most common number of supporting utterances for a sentence may be just one (FIG. 6A). Supporting utterances are referred to as noteworthy utterances in other embodiments described herein.

The data processing system 110 tags each SOAP note sentence with various subsection-specific tags. For example, medications mentioned in the corresponding subsection are annotated with dosage and frequency of use. Similarly, sentences in Review of Systems section include categorical labels describing the symptom being checked and the patient's response mentioned as confirmation or denial. In some embodiments, more granular subsections rather than the coarse sections of SOAP notes are used. However, "subsections" may alternatively be referred to as 'sections' for the sake of simplicity.

Figure 6B:
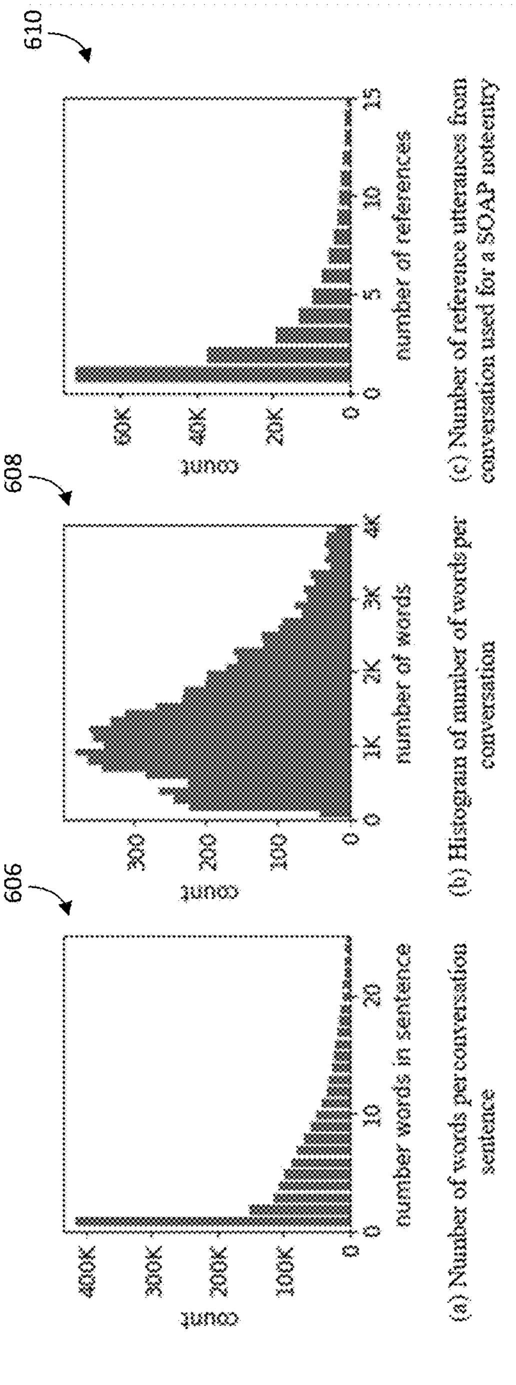

Some embodiments address a dataset of human-transcribed physician-patient conversations. An example dataset represents 2732 cardiologist visits, 2731 family medicine visits, 989 interventional cardiologist visits, and 410 internist visits. Each transcript includes timestamped utterances with speaker labels. FIG. 6B shows graphs 606, 608, and 610 respectively representing a distribution of sentence lengths, a number of words in physician-patient conversations of the dataset, and a number of evidence utterances in it referred by an entry of the corresponding SOAP note. A typical conversation may include of 200-250 utterances. The median utterance may be short (FIG. 6B (a)), possibly due to the high frequency of back-channeling (e.g., "umm-hmm", "okay", etc.). In total, each conversation may include around 1500 words (FIG. 6B (b)). In some embodiments, dataset may include of 6862 datapoints (i.e., physician-patient conversation transcripts with corresponding annotated notes), which may be then divided into train and test sets with sizes 6270 and 592, respectively. To generate training models, 500 points may be set aside as a validation set for tuning hyper-parameters. The number of datapoints and the splits may be the same for both the tasks. In the dataset, each line in a SOAP note may be classified into one of for e.g., 12 total subsections within one of the high-level Subjective, Objective, Assessment, or Plan sections. For example, subsections for the Subjective section may include Subjective: Review of Systems and Subjective: Past Medical History. Each line in a SOAP note may appear alongside structured categorical or numerical metadata. For instance, a SOAP note line about medication (e.g., "Take Aspirin once a day.") may be coupled with structured data for the medication name (e.g., "Aspirin") and the dosage (e.g., "daily"). Each SOAP note line may also be associated with the lines in the transcript that were used as evidence by the annotator to create the line and its metadata. Each SOAP note line with its associated metadata, i.e. SOAP note entry, may use an average of transcript lines as evidence (FIG. 6B (c)). Subsets of information from the dataset described above may be used to design datasets for the relevant diagnosis prediction and review of systems abnormality prediction tasks.

The methods disclosed herein may be performed by data processing system 110. In some embodiments, given a physician-patient conversation, data processing system 110 may extract the mentioned past and present diagnoses of the patient that are relevant to the primary reason for the patient's visit (called the chief complaint). For each conversation, data processing system 110 may create a list of the chief complaint and related medical problems by using categorical tags associated with Subjective and/or a subsection of the SOAP note. All medical problems in the Subjective: Past Medical History subsection are tagged with "HPI" (e.g., History of Present Illness) to signify that they are related to the chief complaint. The medical problem tags present in the Assessment and Plan: Assessment subsection of the SOAP note. Data processing system 110 may then simplify the medical problem tags by converting everything to lowercase, and removing elaborations given in parentheses. For example, data processing system 110 may simplify "hypertension (moderate to severe)" to "hypertension". For each of the 20 most frequent tags retrieved after the previous simplifications, data processing system 110 searches among all medical problems and includes tags that previously had the original tag as a substring. For example, "systolic hypertension" was merged into "hypertension". After following the above procedure on the training and validation set, data processing system 110 selects a given number (e.g., ~15) of the most frequent medical problem tags, as shown in Table 2 below. The data processing system 110 restricts the task to predicting whether each of these medical problems were diagnosed for a patient or not diagnosed for that patient.

TABLE 2

Diagnoses extracted from the train + validation split of the dataset with their number of occurrences

| Diagnosis | Frequency |
|---|---|
| hypertension | 1573 |
| diabetes | 1423 |
| atrial fibrillation | 1335 |
| hypercholesterolemia | 1023 |
| heart failure | 584 |
| myocardial infarction | 386 |
| arthritis | 288 |
| cardiomyopathy | 273 |
| coronary arteriosclerosis | 257 |
| heart disease | 240 |
| chronic obstructive lung disease | 235 |
| dyspnea | 228 |
| asthma | 188 |
| sleep apnea | 185 |
| depression | 148 |

In some embodiments, given physician-patient conversation data, the data processing system 110 determines the organ systems (e.g., respiratory system) for which the patient predicted a symptom (e.g., trouble breathing) for Review of Systems (RoS) Abnormality Prediction. During a patient's visit, the physician performs a RoS process including a review organ systems and potential associated symptoms and asks if the patient is experiencing each symptom. In the dataset SOAP notes, the Subjective: Review of Systems subsection includes annotated observations from the RoS, each including a system, symptom and result. For instance, each annotation includes a system (e.g., "cardiovascular"), an associated symptom (e.g., "chest pain or discomfort") and a result based on patient feedback (e.g., "confirms", "denies"). To reduce sparsity in the data for system/symptom pairs, data processing system 110 determines only systems and whether or not each system may include a confirmed symptom. In some implementations, the data processing system 110 determines only the set of 7 systems for which more than 5% of patients reported abnormalities, for generating predictions, to reduce a processing burden. Example systems are shown in Table 3 below.

TABLE 3

Systems reviewed along with the number of times an abnormality was reported in them in the train + validation split

| System | Frequency |
|---|---|
| cardiovascular | 2245 |
| musculoskeletal | 1924 |
| respiratory | 1401 |
| gastrointestinal | 878 |
| skin | 432 |
| head | 418 |
| neurologic | 385 |

In some embodiments, a single suite of models may be used for the two tasks. A first task includes an input-agnostic baseline. In this process, a best value of each metric is established that can be achieved without using the input (such as an input-agnostic classifier). The behavior of the input-agnostic classifier depends on the metric. To maximize accuracy, the classifier 114 predicts a majority class (usually negative) for all diagnoses. To maximize F1 and recall, the classifier 114 predicts the positive class for all diagnoses. To maximize AUC and precision-at-1, the classifier 114 assigns probabilities to each diagnosis according to their respective prevalence rates.

A medical-entity-matching baseline method uses a traditional string-matching tool. For extracting relevant diagnoses, for each diagnosis, data processing system 110 validates whether that diagnosis is mentioned in the conversation. Since the diagnosis can be expressed in different ways (e.g., "myocardial infarction" has the same meaning as the common term "heart attack"), the data processing system 110 uses a system for tagging medical terms (Quick UMLS) that maps strings to medical entities with a unique ID. For example, "hypertension" and "high blood pressure" are both mapped to the same ID.

In some embodiments, for predicting RoS abnormalities, the baseline predicts that the person has an abnormality in a system if any symptom related to the system is mentioned in the text. The symptoms checked for each system are taken from the RoS tags in the dataset. For example, the cardiovascular system has symptoms like "chest pain or discomfort" and "palpitations, shortness of breath".

For learning based methods, the following classical models may be applied by data processing system 110, including logistic regression, a support vector classifier, multinomial naive Bayes, random forest, and gradient boosting models. The methods disclosed herein use bag-of-words representation of conversations with unigrams and bigrams with term frequency—inverse document frequency (TF-IDF) transforms on the features.

The data processing system 110 is configured to apply neural machine learning models to perform the processes described herein. The methods disclosed herein classified diagnoses and RoS abnormalities as present or not present using two BERT models with word-piece tokenization—one generic, pre-trained BERT model, and one pre-trained BERT model that is fine-tuned on clinical text. Each of the example BERT models are 12-layered with a hidden size of 768. The final hidden state of the [CLS] token is taken as the fixed-dimensional pooled representation of the input sequence. This is fed into a linear layer with sigmoid activation and output size equal to the number of prediction classes (15 for diagnosis prediction and 7 for the RoS abnormality prediction), thus giving us the probability for each class. Since the pre-trained BERT models do not support a sequence length of more than 512 tokens, the methods disclosed herein break up individual conversations into chunks of 512 tokens, pass the chunks independently through BERT and mean-pool their [CLS] representations.

The data processing system 110 can execute hybrid models to determine noteworthy utterances. The long length of the input sequence makes the task difficult for the neural models. The methods disclosed herein try a variety of strategies to pre-filter the contents of the conversation so that only sentences that are more relevant to the task are fed to classifier 114, (such as noteworthy utterances). Three example processes are described for deciding if a sentence is noteworthy. A first process is called UMLS-noteworthy. In this process, the data processing system 110 designates a sentence as noteworthy if the medical tagger finds an entity relevant to the task (e.g., a diagnosis or symptom) as defined in the medical-entity-matching baseline. The second process is called all-noteworthy. For this process, the data processing system 110 deems a sentence in the conversation noteworthy if it was used as evidence for any line in the annotated SOAP note. The classifier 114 is trained to predict the noteworthy sentences given a conversation. The third process is called diagnosis/RoS-noteworthy. In this process, the data processing system 110 defines noteworthy sentences as being only those sentences are deemed noteworthy in the second process that were used as evidence for an entry including the ground truth tags (e.g., diagnosis/RoS abnormality) that are being predicted. In addition to trying out these individual filtering strategies, combinations of these three processes can be performed.

The methods disclosed herein evaluate the performance of models using metrics such as accuracy, area under the receiver-operator characteristics (AUC), F1 score, and precision-at-1. Because the data processing system 100 is performing a multi-label classification task (e.g., predicting positive or negative occurrence of 15 diagnoses), aggregate scores include additional consideration. For both F1 and AUC metrics, the data processing system 110 aggregates scores using both micro- and macro-averaging following the metrics for multi-label diagnosis prediction. Macro-averaging averages scores calculated separately on each label. Micro-averaging pools predictions across labels before calculating a single metric. The data processing system 110 computes precision-at-1 to capture the percentage of times that each model's most confident prediction is correct. This is a frequency with which the most confidently predicted diagnosis actually applies.

Results of Example Models

The performance of all models was aggregated across classes on the tasks of relevant diagnosis prediction, shown in Table 4, and RoS abnormality prediction, shown in Table 5. Predicting RoS abnormality is more difficult than predicting relevant diagnoses, as reflected by the lower values achieved on all metrics. This is because of a variety of symptoms that can be checked for each system. For example, the cardiovascular system has 152 symptoms in our dataset including 'pain in the ribs', 'palpitations', 'increased heart rate' and 'chest ache'. The learning-based model learns to correlate all of these symptoms to the cardiovascular system in addition to predicting whether or not the patient experiences the symptom. For diagnosis prediction, learning of such a correlation may not be needed.

TABLE 4

Aggregate results for the medical diagnosis prediction task.

| Model | Accuracy | Macro-AUC | Macro-F1 | Micro-AU C | Micro-F1 | Precision-at-1 |
|---|---|---|---|---|---|---|
| Input agnostic baseline | 0.9189 | 0.5000 | 0.1414 | 0.7434 | 0.3109 | 0.2027 |
| UMLS Medical Entity Matching | 0.9122 | 0.8147 | 0.5121 | 0.8420 | 0.5833 | 0.5034 |
| Logistic Regression | 0.9417 | 0.8930 | 0.2510 | 0.9317 | 0.5004 | 0.6064 |
| LinearSVC | 0.9395 | 0.8959 | 0.2113 | 0.9354 | 0.4603 | 0.6199 |
| Multinomial NaiveBayes | 0.9269 | 0.7171 | 0.0615 | 0.8296 | 0.1938 | 0.4848 |
| Random Forest | 0.9212 | 0.8868 | 0.0155 | 0.8795 | 0.0541 | 0.5304 |
| Gradient Boosting Classifier | 0.9467 | 0.9181 | 0.5024 | 0.9447 | 0.6514 | 0.5861 |
| BERT | 0.9452 | 0.8953 | 0.4413 | 0.9365 | 0.6009 | 0.6199 |
| CLINICALBERT (CBERT) | 0.9476 | 0.9040 | 0.4573 | 0.9413 | 0.6029 | 0.6300 |
| AN + CBERT | 0.9511 | 0.9222 | 0.4853 | 0.9532 | 0.6561 | 0.6470 |
| DN + CBERT | 0.9551 | 0.9342 | 0.5655 | 0.9616 | 0.7029 | 0.6621 |
| UMLS + CBERT | 0.9519 | 0.8615 | 0.5238 | 0.9290 | 0.6834 | 0.6030 |
| UMLS − AN − CBERT | 0.9541 | 0.9261 | 0.5317 | 0.9588 | 0.6803 | 0.6621 |
| UMLS − DN − CBERT | 0.9510 | 0.9359 | 0.5210 | 0.9593 | 0.6641 | 0.6368 |
| UMLS − F2K − AN + CBERT | 0.9554 | 0.9188 | 0.5599 | 0.9567 | 0.7139 | 0.6487 |
| UMLS + F2K − DN + CBERT | 0.9535 | 0.9354 | 0.5301 | 0.9610 | 0.6911 | 0.6486 |
| ORACLE AN + CBERT | 0.9509 | 0.9418 | 0.5500 | 0.9588 | 0.6789 | 0.6250 |
| ORACLE DN + CBERT | 0.9767 | 0.9771 | 0.7419 | 0.9838 | 0.8456 | 0.7162 |

AN: predicted noteworthy utterances,

DN: utterances predicted to be noteworthy specifically concerning a summary passage discussing diagnoses, F2K: UMLS-extracted noteworthy utterances with added top predicted AN/DN utterances to get K total utterances

TABLE 5

Aggregate results for the RoS abnormality prediction task.

| Model | Accuracy | Macro-AUC | Macro-F1 | Micro-AUC | Micro-F1 | Precision-at-1 |
|---|---|---|---|---|---|---|
| Input agnostic baseline | 0.8677 | 0.5000 | 0.2235 | 0.7024 | 0.3453 | 0.3040 |
| UMLS Medical Entity Matching | 0.4532 | 0.7074 | 0.2797 | 0.7454 | 0.3079 | 0.3226 |
| Logistic Regression | 0.8819 | 0.8050 | 0.2102 | 0.8496 | 0.3506 | 0.3952 |
| LinearSVC | 0.8798 | 0.8093 | 0.1623 | 0.8516 | 0.3025 | 0.3986 |
| Multinomial NaiveBayes | 0.8687 | 0.6183 | 0.0369 | 0.7383 | 0.0653 | 0.3818 |
| Gradient Boosting Classifier | 0.8740 | 0.7949 | 0.2500 | 0.8405 | 0.3324 | 0.4020 |
| Random Forest | 0.8677 | 0.7210 | 0.0000 | 0.7670 | 0.0000 | 0.3412 |
| BERT | 0.8818 | 0.8240 | 0.3304 | 0.8620 | 0.4275 | 0.3986 |
| CLINICALBERT (CBERT) | 0.8784 | 0.8305 | 0.3878 | 0.8667 | 0.4857 | 0.4003 |
| AllNoteworthy + CBERT | 0.8837 | 0.8491 | 0.3560 | 0.8801 | 0.4761 | 0.4274 |
| ROSNoteworthy + CBERT | 0.8861 | 0.8391 | 0.3720 | 0.8788 | 0.4925 | 0.4054 |
| UMLS + CBERT | 0.8769 | 0.8036 | 0.3421 | 0.8464 | 0.4457 | 0.3902 |
| UMLS + AN + CBERT | 0.8868 | 0.8252 | 0.3039 | 0.8626 | 0.4515 | 0.4139 |
| UMLS + RN + CBERT | 0.8810 | 0.8390 | 0.3122 | 0.8745 | 0.4152 | 0.3902 |
| UMLS + F2K − AN + CBERT | 0.8834 | 0.8169 | 0.2385 | 0.8585 | 0.3894 | 0.4189 |
| UMLS + F2K − RN + CBERT | 0.8827 | 0.8595 | 0.3987 | 0.8895 | 0.5308 | 0.4291 |

TABLE 5-continued

| Aggregate results for the RoS abnormality prediction task. | | | | | | |
|---|---|---|---|---|---|---|
| Model | Accuracy | Macro-AUC | Macro-F1 | Micro-AUC | Micro-F1 | Precision-at-1 |
| ORACLE AN + CBERT | 0.8846 | 0.8535 | 0.3662 | 0.8841 | 0.5062 | 0.4375 |
| ORACLE RN + CBERT | 0.9454 | 0.9595 | 0.7235 | 0.9703 | 0.7847 | 0.4966 |

AN: predicted noteworthy utterances,
RN: utterances predicted to be noteworthy specifically concerning a summary passage discussing review of systems,
F2K: UMLS-extracted noteworthy utterances with added top predicted AN/RN utterances to get K total utterances In some embodiments, for diagnosis prediction, the medical-entity-matching baseline model achieves better F1 scores than many of the classical models, which is due to a high recall at the cost of lower precision (0.76 and 0.47 respectively when micro-averaged). The high recall and low precision together demonstrate that if a diagnosis has been made for the patient, the diagnosis is often directly mentioned in the conversation but the con-verse is not true. Among the BERT-based models, a modest improvement in F1 and precision-at-1, when using ClinicalBERT instead of the common BERT. This is because the former model is fine-tuned on clinical text. Using predicted noteworthy sentences from the transcript instead of all of the transcript generally led to an improvement in performance.

In some embodiments, for diagnosis prediction, using a model that uses only predicted diagnosis-noteworthy sentences rather than all-noteworthy sentences performs the best for a majority of the metrics. For RoS abnormality prediction, the trend reverses and using predicted RoS-noteworthy sentences performs worse than using predicted All Noteworthy sentences from the transcript. The methods disclosed herein train on ORACLE noteworthy sentences, to achieve a precision-at-1 of 0.72 for diagnosis prediction and 0.50 for RoS abnormality prediction. Note that the maximum achievable precision-at-1 on the diagnosis prediction task is 0.7584 and for the RoS abnormality prediction task it is 0.5811, because the patients do not always have one of the diagnoses or RoS abnormalities are concerned with.

In some embodiments, the average number of UMLS-noteworthy sentences extracted by the extraction module 112 for diagnosis prediction and RoS abnormality prediction tasks is 4.42 and 5.51 respectively out of an average of 215.14 total sentences. The methods disclosed herein, train BERT on only the UMLS-noteworthy sentences, on a union of UMLS-noteworthy sentences and predicted all/task-specific noteworthy sentences, and a FillUptoK(F2K) variant where the union is taken but only the top-predicted all/task-specific noteworthy sentences are added until a total of K sentences to be fed into BERT is reached, where K is a hyper-parameter. The last model achieves the best results for RoS ab-normality prediction when the UMLS-noteworthy sentences with the top-predicted RoS-noteworthy sentences are pooled.

Figure 7:
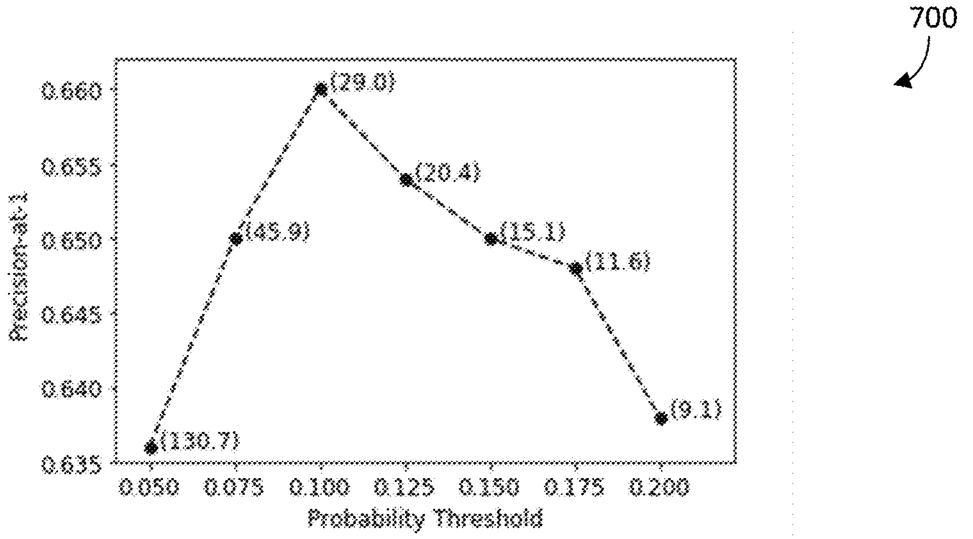
FIG. 7 is an exemplary graphical representation, consistent with disclosed embodiments.

For both tasks, it is possible to use a small fraction of the transcript and still obtain performance comparable to models that use all of it. For the task of diagnosis prediction, the UMLS-noteworthy sentences only make up 2.1% of total sentences in a conversation on average, but using just them with the ClinicalBERT model still achieves higher F1 scores than all classical ML models which use the entire conversation. In some embodiments, an experiment may be carried out to observe the correlation between number of words input into the ClinicalBERT model and the performance achieved. To do this, threshold probability is varied for the noteworthy utterance classifier in the Diagnosis–noteworthy+ClinicalBERT model. Fewer noteworthy sentences are extracted and passed to ClinicalBERT as the threshold goes up. The performance increases with a decrease in the number of filtered sentences and then goes down (FIG. 7). The best performance is achieved when an average of 29 utterances for each is passed.

Performance on binary prediction tasks besides calculating the aggregate performance of our models, the methods discussed herein also compute the performance of our best model for each task at the binary prediction of each diagnosis/RoS abnormality, as shown in Table 6 and Table 7.

TABLE 6

Performance of our best diagnosis prediction model (DN + CBERT) at predicting individual diagnoses. CP@1: contribution to precision-at-1, the fraction of times a disease was a correct top prediction

| Disease | Prevalence rate | Precision | Recall | F1 | Accuracy | AUC | CP@1 |
|---|---|---|---|---|---|---|---|
| atrial fibrillation | 0.2568 | 0.8667 | 0.9408 | 0.9022 | 0.9476 | 0.9773 | 0.3597 |
| hypertension | 0.2027 | 0.6667 | 0.4833 | 0.5604 | 0.8463 | 0.8817 | 0.0995 |
| diabetes | 0.1959 | 0.8411 | 0.7759 | 0.8072 | 0.9274 | 0.9586 | 0.1837 |
| hypercholesterolemia | 0.1216 | 0.5694 | 0.5694 | 0.5694 | 0.8953 | 0.9246 | 0.0740 |
| heart failure | 0.1014 | 0.8049 | 0.5500 | 0.6535 | 0.9409 | 0.9692 | 0.0638 |
| myocardial infarction | 0.0861 | 0.8571 | 0.8235 | 0.8400 | 0.9730 | 0.9857 | 0.0995 |
| coronary arteriosclerosis | 0.0372 | 0.3846 | 0.2273 | 0.2857 | 0.9578 | 0.8307 | 0.0051 |
| chronic obstructive lung disease | 0.0372 | 0.7391 | 0.7727 | 0.7556 | 0.9814 | 0.9665 | 0.0281 |
| dyspnea | 0.0304 | 0.5000 | 0.0556 | 0.1000 | 0.9696 | 0.9068 | 0.0077 |
| depression | 0.0304 | 0.6471 | 0.6111 | 0.6286 | 0.9780 | 0.9555 | 0.0230 |
| asthma | 0.0287 | 0.8462 | 0.6471 | 0.7333 | 0.9865 | 0.9951 | 0.0230 |
| cardiomyopathy | 0.0236 | 0.7143 | 0.7143 | 0.7143 | 0.9865 | 0.9779 | 0.0128 |
| heart disease | 0.0236 | 0.0000 | 0.0000 | 0.0000 | 0.9764 | 0.7058 | 0.0026 |
| arthritis | 0.0220 | 0.3636 | 0.3077 | 0.3333 | 0.9730 | 0.9843 | 0.0128 |
| sleep apnea | 0.0186 | 0.6667 | 0.5455 | 0.6000 | 0.9865 | 0.9937 | 0.0051 |

TABLE 7

Performance of our best RoS abnormality prediction model (UMLS + F2K − RN + CBERT) at predicting abnormalities in each system. CP@1: contribution to precision-at-1, the fraction of times an RoS abnormality was a correct top prediction

| System | Prevalence rate | Precision | Recall | F1 | Accuracy | AUC | CP@1 |
|---|---|---|---|---|---|---|---|
| cardiovascular | 0.3041 | 0.5867 | 0.7333 | 0.6519 | 0.7618 | 0.8475 | 0.5079 |
| musculoskeletal | 0.2010 | 0.5893 | 0.5546 | 0.5714 | 0.8328 | 0.8579 | 0.2402 |
| respiratory | 0.1571 | 0.5231 | 0.3656 | 0.4304 | 0.8480 | 0.8639 | 0.1063 |
| gastrointestinal | 0.0845 | 0.5217 | 0.4800 | 0.5000 | 0.9189 | 0.8636 | 0.0669 |
| head | 0.0828 | 0.4412 | 0.3061 | 0.3614 | 0.9105 | 0.9252 | 0.0591 |
| neurologic | 0.0574 | 0.0000 | 0.0000 | 0.0000 | 0.9426 | 0.7864 | 0.0000 |
| skin | 0.0389 | 0.6667 | 0.1739 | 0.2759 | 0.9645 | 0.8719 | 0.0197 |

In some situations, diagnoses that are more common are detected with higher accuracy and more frequently. One exception is hypertension, which has a low recall and precision despite affecting around 20% of the patients. The instances of hypertension that are not identified by the model show that hypertension is rarely mentioned explicitly during conversation. Instead, hypertension is generally inferred by values of blood pressure readings and phrases like "that blood pressure seems to creep up a little bit." The indirect way in which hypertension is mentioned increases a difficult of detection. In contrast, atrial fibrillation is typically mentioned explicitly during conversation. This is why even the medical-entity-matching baseline achieves a high recall of 0.83 at predicting atrial fibrillation. The medical-entity-matching baseline model has the worst performance for predicting heart disease. In some situations, this is due to a combination of low frequency and the generic nature of the class. The heart disease tag is used in miscellaneous situations like genetic defect, weakness in heart's function, or pain related to stent placement.

In some embodiments, contribution to precision-at-1 for each class for both tasks is calculated. This gives a sense of how often a diagnosis/RoS abnormality becomes a top prediction for a given model. In some embodiments, a situation where only the most frequent diagnoses/RoS abnormalities are predicted with the highest probability and the rarer classes do not get any representation in the top prediction may be avoided. The contribution to precision-at-1 is defined for a class as the number of times it was a correct top prediction divided by the total number of correct top predictions made by the model. For both tasks, contribution to precision-at-1 is roughly in proportion to the prevalence rate of each diagnosis, as shown in Table 6 and Table 7. The model predicts even the rarer diagnoses with enough confidence for those rarer diagnoses to show up as top predictions. The hyper-parameters of each learning-based model are determined by tuning over the validation set.

In this example, the BERT models have a learning rate of 0.00002. The probability threshold for predicting noteworthy sentences may be tuned. The optimal threshold was 0.4 for predicting all noteworthy sentences, 0.1 for predicting diagnosis-related noteworthy sentences and 0.02 for predicting RoS-related noteworthy sentences. Among the FillUpToK predictors for diagnosis prediction, the one using All-Noteworthy sentences had K=50 and the one using diagnosis-noteworthy sentences has K=15. For the FillUpToK predictors used for RoS abnormality prediction, the one using all-noteworthy sentences had K=50 and the predictor using RoS-noteworthy sentences had K=20.

The noteworthy sentence extractors are logistic regression models trained, validated and tested on the same splits of the dataset as the other models. All models are L2-regularized with the regularization constant equal to 1. The AUC scores for the classifiers extracting all, diagnosis-related, and RoS-related noteworthy sentences are 0.6959, 0.6689 and 0.7789 respectively.

In some embodiments, four different approaches for generating SOAP notes may be used by data processing system 110. The four different approaches include four algorithms designed to decompose the chunks of data into two different phases—extractive and abstractive, with each method shifting work among the two phases of the summarization pipeline.

Algorithm List

Algorithm 1: FullConversationToFullSummary

```
U ← sequence of utterances from conversation
N ← F1 (U)
return N
```

Algorithm 2: SupportingUtterancesToFullSummary

```
U - sequence of utterances from conversation
S - E1(U)
N - F2(S)
return N
```

Algorithm 3: SectionwiseSummaryGeneration

```
U - sequence of utterances from conversation
P - sequence of sections in a SOAP note
for section ∈ P do
 |  S_section - E2(U, section)
 |  N_section - F3(S_section, section)
end
N -     N_section
     section∈P
return N
```

Algorithm 4: SentencewiseSummaryGeneration

```
U - sequenceofutterancesfromconversation
P - sequence of sections in a SOAP note
for section ∈ P do
 |  S_section - E2(U, section)
 |  C_section - C(S_section)
```

-continued

Algorithm 4: SentencewiseSummaryGeneration

```
|   sort C_section using timestamp of earliest supporting utterance in
    each cluster
|   N_section - φ
|   for Z_cluster ∈ C_section do
|     |   S_cluster - F_4(Z_cluster, section)
|     |   N_section - N_section ∪ S_cluster
|   end
|
end
N -        N_section
      section∈P
return N
```

Algorithm 1 takes an end-to-end approach, generating the entire SOAP note from the entire conversation in one shot. Algorithm 2 first predicts all the noteworthy utterances in the conversation (without regard to the associated section) and then generates the entire SOAP note in one shot from only those utterances. Algorithm 3 generates the SOAP note by generating one section at a time, using only the extracted noteworthy utterances that are predicted to be relevant to that section. Algorithm 4 attempts to group together the set of noteworthy utterances associated with each summary sentence. The data processing system 110 clusters together section-specific noteworthy utterances, and then generates each section one sentence at a time, conditioning each on the associated cluster of sentences.

Each of these pipelines still allows a set of several choices of the specific models to employ for each subtask. The data processing system 110 can execute several different models for each of the subtasks. For the abstractive modules of Algorithm 1 and Algorithm 2, denoted by $F_1$ and $F_2$ respectively, data processing system 110 may use a pointer generator network. The abstractive modules of Algorithm 3 ($F_3$) and Algorithm 3 ($F_4$) are modeled as conditioned pointer-generator networks that condition on the section for which the summary is to be generated as described below in detail.

For the utterance extractor used in Algorithm 2, denoted by $\varepsilon_1$, data processing system 110 trains a logistic regression baseline and a hierarchical LSTM model. Algorithm 3 and Algorithm 4 both use the same extractor denoted by $\varepsilon_2$ that predicts whether a given utterance is noteworthy with respect to each section. For $\varepsilon_2$, with logistic regression, a hierarchical LSTM model, and a BERT-LSTM with multi-label output is used.

The architecture of the hierarchical LSTM and BERT-LSTM models are as follows. For the utterance extractor used in Algorithm 2, denoted by $\varepsilon_1$, data processing system 110 trains a logistic regression baseline and a hierarchical LSTM model. Algorithm 3 and Algorithm 4 both use the same extractor denoted by $\varepsilon_2$ that predicts whether a given utterance is noteworthy with respect to each section. For $\varepsilon_2$, logistic regression, a hierarchical LSTM model, and a BERT-LSTM with multi-label output is used.

For the clustering module used in Algorithm 4, C a clustering heuristic that groups together supporting utterances whose distance from each other is below a threshold $\tau$ is used. Since each cluster necessarily produces one sentence in the SOAP note, having too many or too few clusters can make the SOAP note too long or short respectively. Therefore, the value of the hyper-parameter $\tau$ is tuned on the validation set to produce approximately the same number of clusters over the entire validation data set as present in the ground truth. In the dataset, approximately 38% of clusters of noteworthy utterances are singleton (FIG. 6A), and among the remaining clusters including multiple noteworthy utterances, all of the utterances are contiguous in 82% of the cases. Hence this clustering heuristic works quite well. To verify it quantitatively, an experiment is performed, where the heuristic is used to cluster the oracle noteworthy utterances for each section, and then the clusters are used to generate the SOAP notes as outlined in Algorithm 4. The performance achieved on all ROUGE metrics was only about 1 point below the highest achievable score (mentioned in Table 8 below) using oracle cluster annotations.

The data processing system 110 is configured to use the pointer-generator network for Algorithm 1 and 2. The pointer-generator network embeds the input sequence of words $w_1, w_2, \ldots w_n$ into learnt embeddings $e_1, e_2, \ldots e_n$ by a lookup table. These values are passed through a bidirectional LSTM encoder to get the input encodings. This is shown in Equation (1).

$$\{h_1, h_2, \ldots, h_n\} = BiLSTM_{enc}(\{e_1, e_2, \ldots, e_n\}) \quad (1)$$

The output is generated word by word in multiple timesteps using an LSTM decoder augmented with an attention mechanism. At each timestep, the state $s_t$ of the decoder LSTMdec is used to calculate an attention distribution at across the input words. The attention distribution is used to take a weighted average of the input encodings to give a context vector h*t, which is then passed through linear layers with softmax activation to generate a distribution $P_{vocab}$ over words to be generated next. $W_h$, $W_s$, $b_{attn}$, V', V, b, b' and v are parameters that are learnt.

$$e_i^t = v^T \tanh(W_h h_i + W_s s_t + b_{attn} \quad (2)$$

$$a^t = \text{softmax}(e^t) \quad (3)$$

$$h_t^* = \sum_{i=1}^{n} a_i^t h_i \quad (4)$$

$$P_{vocab} = \text{softmax}(V'(V[s_t; h_t^*] + b) + b' \quad (5)$$

$$P_{copy} = \sum_{i=1}^{n} a_i^t \mathbb{I}(w_i, w) \quad (6)$$

While $P_{vocab}$ is the probability of generating a new word, the model also calculates a distribution $R_{copy}$ over words to be copied from the source text. The probability of copying a word w from the source text at timestep t is given by the aggregate attention received by all occurrences of w in the input.

$$P_{copy} = \sum_{i=1}^{n} a_i^t II(w_i, w), \quad (6)$$

where I is the indicator function that gives 1 if both its arguments are equal and 0 otherwise. The output of the model is a weighted combination of $P_{vocab}$ and $R_{copy}$. The affinity of the model's output towards generating a new word versus copying a word from the input is given by $p_{gen}$ computed as in equation 7, where $w_s$, $w_n$*, $w_x$, $b_{gen}$ are learnt parameters, and $x_t$ is the input to $LSTM_{dec}$ at time step t, which is a concatenation of $h^*_t$ 1 and the word embedding for the previous timestep's output passed through a linear layer. The final output is the word distribution P (w) as given in Equation 8.

$$p_{gen} = \sigma(w_h^T \cdot h_t^* + w_s^T s_t + w_\Sigma^T x_t + b_{gen}) \quad (7)$$

$$P(w) = p_{gen} P_{vocab}(w) + (1 - p_{gen}) P_{copy}(w) \quad (8)$$

The data processing system 110 uses a modification of pointer-generator network for algorithms 3 and 4, where extra information is input to the network in the form of the section for which the summary is being generated. For this approach, z represents the section for which the summary is being generated. The network uses a new lookup table to embed the section into an embedding $e^z$. The section embedding is concatenated to each input word embedding fed into the encoder as given in equation 9. The section embedding is also appended to the inputs of the decoder LSTM in the same fashion.

$$\{h_1, h_2, \ldots, h_n\} = BiLSTM_{enc}(\{[e_1; e^z], [e_2; e^z], \ldots [e_n; e^z]\}) \quad (9)$$

The data processing system 110 uses a hierarchical LSTM classifier to classify conversation utterances as noteworthy or not. For algorithm 2, the data processing system 110 uses the LSTM as a binary classifier, and for algorithms 3 and 4, the data processing system 110 uses the LSTM as a multi-label classifier where an utterance can be classified as noteworthy or not with respect to each among the multiple sections of the SOAP note.

Given an input conversation with utterances $\{u_1, u_2, \ldots, u_n\}$ where each utterance is represented by a sequence of words $u_j = \{w_1, w_2, \ldots, w_n\}$, a representation $h_j$ of each utterance $u_j$ is computed. This is done by embedding the words of each $u_j$ into embeddings $\{e_1, e_2, \ldots, e_n\}$ using an embedding lookup table. The data processing system 110 computes each utterance's representation h* as the meanpooled output of a bidirectional LSTM given the embeddings as the input.

$$\{h_1, h_2, \ldots, h_{n_j}\} = BiLSTM_{utterance}(\{e_1, e_2, \ldots, e_{n_j}\}) \quad (10)$$

$$h^* = \sum_{i=1}^{n_j} h_i \quad (11)$$

Given the representations for the sequence of utterances as h*1, h*2, . . . , h*n, the data processing system 110 passes the utterances through a bidirectional LSTM to incorporate the context across different utterances before predicting whether each utterance is noteworthy or not. The resulting output representation $z_i$ for each utterance is passed through a sigmoid-activated linear layer to get the output $p_i$. In Algorithm 2, the data processing system 110 is configured to predict whether an utterance is noteworthy (for any section), pi is a scalar. For Algorithms 3 and 4, pi is a vector, where $p_j$ represents the probability of it being a noteworthy utterance with respect to the $j^{th}$ section.

$$\{z_1, z_2, \ldots, z_n\} = BiLSTM_{context}(\{h_1^*, h_2^*, \ldots, h_n^*\}) \quad (12)$$

$$o_i = W_{proj} z_i \quad (13)$$

$$p_i = \sigma(o_i) \quad (14)$$

The data processing system executes a BERT-LSTM classifier to categorize utterances into different SOAP note sections. Its usage with different summarization algorithms mirrors that of the hierarchical LSTM. Each token in the utterance is passed through the BERT encoder to obtain a contextualized representation, i.e., $$\left[h_{i1}^{BERT}, h_{i2}^{BERT}, \ldots, h_{im}^{*BERT}\right],$$

where $h_{ij}$ represents BERT-encoding of $j^{th}$ token of $u_i$. The utterance-level representation is obtained by MEAN pooling the contextualized token embeddings.

$$h_i^{BERT} = \frac{1}{m} \sum_{j=1}^{m} h_{ij}^{BERT} \quad (15)$$

Apart from encoding the text of an utterance, the data processing system 110 uses side information like speaker identity and utterance's position in the conversation. Additionally, conversations usually involve multiple speakers, each of them playing a specific role in the goal of that interaction. For instance, diagnosis and medications are likely to be narrated by the doctor rather than the patient. The speaker identity is used to allow the model to condition representations on the speaker of the utterance. Additionally, clinical conversations generally follow a pattern where SOAP note sections, such as symptoms, past medical history and chief complaints, are more likely to be discussed earlier in the dialog; medications and diagnosis are presented in the middle or around the culmination. Positional information in our model by partitioning all the utterances in a conversation into k equal parts based on their position. For instance, if k=5 and number of utterances is 20 then initial 4 belongs to $0^{th}$ partition and the next 4 belongs to $1^{st}$ partition and so on.

Both signals are mapped to separate d-dimensional embeddings, which are concatenated with the utterance embedding, and learned during training:

$$h_i^* = \left[h_i^{BERT}, h_i^{SPK}, h_i^{POS}\right].$$

The resulting utterance-level feature vectors are passed through a bidirectional LSTM to incorporate context across different utterances. Similar to the hierarchical LSTM, the resulting output representation $z_i$ is passed through a fully-connected layer followed by a sigmoid layer to get the final logit $p_i$. Domain-specific supervised fine-tuning of BERT encoder significantly improves performance in a variety of tasks. Following this, the data processing system 110 performs end-to-end fine-tuning of the BERT-LSTM on our training dataset.

For the hierarchical LSTM classifier, an example word embedding size is 128, and both bidirectional LSTMs have a hidden size of 256. For the BERT-LSTM classifier, the BERT embeddings are initialized from BERT-base-uncased (768 dimensions). LSTMs in either direction have a hidden-layer of size 512. Speaker and Position (k=4) information are initialized as 8 and 4 dimensional learnable embedding vectors respectively and the entire model is optimized end-to-end with a learning-rate of 0.001. The pointer-generator models have a word embedding size of 128, and a hidden size of 256 for both the encoder and the decoder. The section embeddings used in section-conditioned pointer-generator network have 32 dimensions.

The data processing system 110 uses beam search was used to generate the output for both these models with a beam size of 4. For the vanilla pointer-generator model used in Algorithm 1 and 2, we modified the beam search procedure to make sure that all the SOAP note sections are generated in proper order. To do this, the data processing system 110 initiates the beam search procedure by feeding the header of the first section (chief complaint). Whenever the model predicts a section header as next word and it shows up in a beam, the data processing system 110 determines whether the header is the next section to be generated. If not, the data processing system 110 replaces the header with the header of the correct next section. Any end-of-summary tokens generated before all the sections have been produced are also replaced similarly. Producing all sections means that the headers for each section have to be generated, and a section can be left empty by starting the next section immediately after generating the previous section header.

In an example experiment, the data processing system 110 executed using two baselines. The first baseline includes a random baseline where given a conversation. The data processing system 110 outputs a randomly chosen SOAP note from our training set as the output. The data processing system 110 runs the experiment 25 times and report the average ROUGE scores obtained. The standard deviation was less than 0.003 for each variant of ROUGE. The second baseline includes an extractive baseline. All the noteworthy utterances from the conversation are presented as the SOAP note. The data processing system 110 uses oracle noteworthy utterances for this baseline to get the best ROUGE scores that can be achieved by having an output that has all the correctly chosen information from the conversation. The output is not expressed in the form and language of a SOAP note. Both baselines give similar performance and are vastly outperformed by all algorithms described previously (e.g., Algorithms 1-4).

The data processing system 110 trains the abstractive summarization models for algorithms 2, 3 4 with the ground-truth noteworthy utterances as inputs. While testing, the data processing system 110 receives, as input, predicted noteworthy utterances. This is because it is not known apriori which utterances are noteworthy in a new unseen conversation. However, to get an estimate of the upper bound on the performance for a perfect classifier for noteworthy utterances, the data processing system 110 is tested with oracle noteworthy utterances. All three algorithms that make use of noteworthy utterances outperform Algorithm 1, which takes an end-to-end approach to generate the full SOAP note from the full conversation. The ROUGE scores increase monotonically from Algorithm 1 to Algorithm 4. The best model using noteworthy utterances improves over Algorithm 1 by around 16, 14 and 23 points on ROUGE-1, ROUGE-2 and ROUGE-L respectively, demonstrating the performance gains that can be made with perfect noteworthy utterance classifiers.

Four models are used to predict noteworthy utterances. The first is a logistic regression baseline modeled on TF-IDF transformed bag of words representation of each utterance. Separate logistic regression models are used for each section of the SOAP note in Algorithm 3 and Algorithm 4. The second model uses a bidirectional LSTM to encode each utterance as the meanpooled representation of its words, and using it jointly predicts the probabilities of it being a noteworthy utterance for each of the SOAP note sections. These two models make the predictions for each utterance independently and do not take the context present in the sequence of utterances into account. To take the context into account, a hierarchical LSTM architecture is used as previously described. There is a uniform trend in all the classification metrics as shown in Table 3, with the bidirectional LSTM model performing slightly better than logistic regression, and the hierarchical LSTM performing much better than both. This shows that for predicting the noteworthiness of an utterance, incorporate the context from neighboring utterances improves performance.

TABLE 8

ROUGE scores for different methods

| Method | ROUGE-1 | ROUGE-2 | ROUGE-L |
|---|---|---|---|
| Random Note Baseline | 0.3164 | 0.1000 | 0.2239 |
| Oracle Supporting Sentences | 0.3225 | 0.1127 | 0.2053 |
| FullConversationToFullSummary | 0.4894 | 0.2423 | 0.3548 |
| SupportingUtterancesToFullSummary (Oracle) | 0.5289 | 0.2692 | 0.3846 |
| SectionwiseSummaryGeneration (Oracle) | 0.5825 | 0.3294 | 0.4876 |
| SentencewiseSummaryGeneration (Oracle) | 0.6524 | 0.3891 | 0.5824 |
| SupportingUtterancesToFullSummary (LR) | 0.4750 | 0.2274 | 0.3419 |
| SectionwiseSummaryGeneration (LR) | 0.4880 | 0.2385 | 0.3562 |
| SentencewiseSummaryGeneration (LR) | 0.5289 | 0.2671 | 0.3799 |
| SupportingUtterancesToFullSummary (LSTM) | 0.4929 | 0.2402 | 0.3524 |
| SectionwiseSummaryGeneration (LSTM) | 0.4926 | 0.2414 | 0.3591 |
| SentencewiseSummaryGeneration (LSTM) | 0.5349 | 0.2736 | 0.3860 |
| SupportingUtterancesToFullSummary (hi-LSTM) | 0.4972 | 0.2441 | 0.3583 |
| SectionwiseSummaryGeneration (hi-LSTM) | 0.5119 | 0.2529 | 0.3774 |
| SentencewiseSummaryGeneration (hi-LSTM) | 0.5561 | 0.2873 | 0.4072 |
| SectionwiseSummaryGeneration(BERT-LSTM) | 0.5222 | 0.2636 | 0.3920 |
| SentencewiseSummaryGeneration (BERT-LSTM) | 0.5648 | 0.2960 | 0.4182 |

The performance on the SOAP note generation task drops when using predicted noteworthy utterances instead of oracle ones, as shown in Table 8. When using logistic regression model for extracting noteworthy utterances, Algorithm 2 and 3 no longer do better than Algorithm 1. However, generating the SOAP note sentence wise (Algorithm 4) manages to outperform Algorithm 1 even with the relatively poor performance of these noteworthy utterance extractors. Since Algorithms 3 and 4 use exactly same extracted noteworthy utterances, the superior performance of the latter suggests an inherent benefit in generating the SOAP note one sentence at a time. Using the noteworthy utterances extracted by a BERT-LSTM causes better performance and Algorithm 4 achieves the best ROUGE scores outperforming Algorithm 1 by a significant margin including an improvement of about 7 points in ROUGE-1.

The quality of generated summaries varies across different sections of the SOAP note. Sections that are less frequent in the dataset such as allergies and healthcare complaints have relatively lower ROUGE scores, likely because there is not enough training data. One notable exception is with respect to immunizations, which occurs sparsely in the dataset but has the highest ROUGE score amongst all sections. This is because the conversation is mostly about a patient getting a flu shot (e.g., 20 out of the 25 times it occurs in the test dataset), and the model generates the immunization result.

TABLE 9

Aggregate performance metrics for multi label classification of supporting utterances across different SOAP note sections

| Metric | Logistic Regression | LSTM | Hi-LSTM | BERT-LSTM |
|---|---|---|---|---|
| Accuracy | 0.9604 | 0.9611 | 0.9650 | 0.9675 |
| Macro-AUC | 0.7814 | 0.7934 | 0.9008 | 0.9086 |
| Macro-F1 | 0.2952 | 0.3102 | 0.3863 | 0.4075 |
| Macro-Precision | 0.3033 | 0.3229 | 0.4088 | 0.4388 |
| Macro-Recall | 0.2924 | 0.3048 | 0.3719 | 0.3852 |
| Micro-AUC | 0.8732 | 0.8762 | 0.9271 | 0.9343 |
| Micro-F1 | 0.3127 | 0.3293 | 0.3960 | 0.4106 |
| Micro-Precision | 0.3182 | 0.3326 | 0.4006 | 0.4392 |
| Micro-Recall | 0.3075 | 0.3261 | 0.3916 | 0.3855 |

In the example experiment, the SOAP notes produced by Algorithm 1 had a lower fraction of novel ngrams (ngrams that do not occur in the input conversation) compared to Algorithm 4, as shown in Tables 10-11. The fraction of novel ngrams in a summary is used to measure how abstractive the summary is. The result suggests that Algorithm 4 produces more abstractive summaries than Algorithm 1 which has a higher tendency to copy sequences of words as-is from the conversation.

TABLE 10

Average ROUGE scores for each section of SOAP note (N-number of test datapoints with the section populated. L-average number of words to ground truth)

| Subsection | ROUGE-1 | ROUGE-2 | ROUGE-L | N | L |
|---|---|---|---|---|---|
| chief complaint | 0.4105 | 0.1724 | 0.3963 | 592 | 11.4 |
| review of systems | 0.4184 | 0.1989 | 0.3883 | 514 | 29.2 |
| past medical history | 0.4523 | 0.2459 | 0.4255 | 547 | 17.8 |
| past surgical history | 0.4031 | 0.1680 | 0.3865 | 230 | 10.3 |
| family medical history | 0.3521 | 0.1813 | 0.3358 | 72 | 16.1 |
| social history | 0.3831 | 0.1580 | 0.3742 | 97 | 10.3 |
| medications | 0.5414 | 0.3124 | 0.5100 | 549 | 15.2 |
| allergies | 0.1971 | 0.1048 | 0.1971 | 21 | 8.5 |
| miscellaneous | 0.2459 | 0.945 | 0.2306 | 415 | 34.4 |
| immunizations | 0.5707 | 0.4618 | 0.5646 | 25 | 7.3 |
| laboratory and imaging results | 0.4699 | 0.2415 | 0.4452 | 448 | 19.3 |
| assessment | 0.3390 | 0.1149 | 0.2651 | 570 | 132.4 |
| diagnostics and appointments | 0.4372 | 0.2489 | 0.4171 | 488 | 17.6 |
| prescriptions and therapeutics | 0.3970 | 0.1748 | 0.3677 | 446 | 18.7 |
| healthcare complaints | 0.1811 | 0.0279 | 0.1775 | 43 | 16.7 |

TABLE 11

Fraction of novel N-grams in the ground truth SOAP note and the outputs of different algorithms with respect to the corresponding conversation

| N | 1 | 2 | 3 | 5 | 7 | 10 |
|---|---|---|---|---|---|---|
| Ground truth | 0.2409 | 0.6779 | 0.8522 | 0.9501 | 0.9773 | 0.9902 |
| Algorithm 4 | 0.1275 | 0.4509 | 0.6522 | 0.8287 | 0.9111 | 0.9653 |
| Algorithm 1 | 0.0902 | 0.3579 | 0.5575 | 0.7550 | 0.8514 | 0.9220 |

Figure 8:
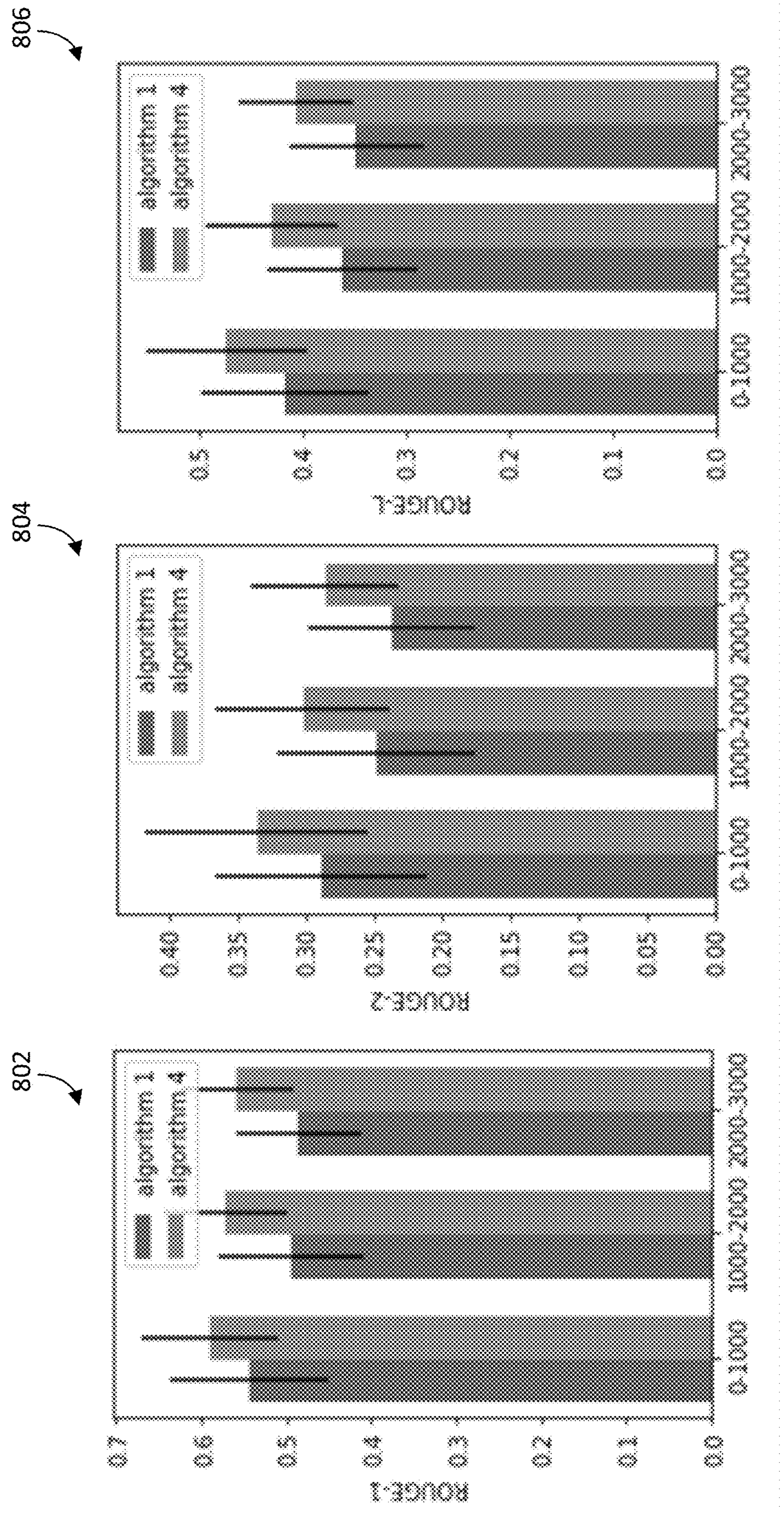
FIG. 8 is an exemplary graphical representation, consistent with disclosed embodiments.

Algorithm 1 generates longer outputs, such as 358 words per SOAP note on an average, compared to Algorithm 4, which generated an average of 250 words per SOAP note. The summaries generated by Algorithm 1 exhibits high degree of repetition in the generated sentences and phrases even after the pointer-generator network was fine-tuned with coverage loss. Both Algorithm 1 and Algorithm 4 perform better on shorter conversations, as measured by ROUGE scores. FIG. 8 shows graphs 802, 804, and 806 representing ROUGE score outputs averaged over different lengths of input conversations. The difference is more visible for variants of ROUGE comparing longer sequences of text.

The SOAP notes generated were compared with the input conversation and the ground truth. FIG. 9 shows a table 900 representing summaries of smaller noteworthy utterance clusters generated by the abstractive module of Algorithm 4. The input clusters are taken from the test dataset and obfuscated by changing sensitive data such as symptoms, medications, dosages and lab readings due to privacy concerns.

The conditioned pointer-generator model used in Algorithm 4 learns what kind information is relevant for each section. Hence, given a cluster of supporting utterances, the data processing system 110 generates different summaries for multiple sections using the model. For example, given the same supporting utterances discussing the patient's usage of Lisinopril for low blood pressure, the model generates "low blood pressure" in the review of systems section, "Lisinopril" in medications, and "discussed that lisinopril is a good pill for blood pressure" in the assessment section. However, in a scenario where the abstractive summarization model is invoked to generate a summary for a section while feeding in supporting utterances that do not have anything relevant to that section can lead to completely unrelated made-up facts that are not mentioned in the conversation. For example, sometimes the model fabricates information such as saying the patient is a non-smoker in the social history section, or that the patient has taken a flu shot in the immunizations section. Hence, the performance of the summarization model depends crucially on the ability of the noteworthy utterance extractor used to classify the extracted utterances to the correct section.

The conditioned pointer-generator model sometimes produces new inferred information that is not mentioned in the conversation but is nevertheless correct. One example is the ability of the model, when executed by the data processing system 110, to predict the diseases that the person has by looking at the medicines being taken. In one instance, the data processing system 110 generated an output that the patient has a history of heart disease, although heart disease or even heart was never mentioned in the conversation. Algorithm 4 used a noteworthy utterance that mentioned that the patient takes the medicine digoxin, which is used for heart disease, to generate that line mentioning the disease in the SOAP note. In another example, the data processing system 110 generated a past medical history of high cholesterol by determining that the patient was on pravastatin. In another scenario, supporting utterances reflected the doctor explaining to the patient that he/she has leaky heart valves which are causing shortness of breath. The data processing system 110 generated a sentence diagnostics and appointments section saying "check valves". While the doctor might not have suggested the diagnostic procedure during the visit, this result shows that non-trivial correlations are learned by the model.

Figure 10:
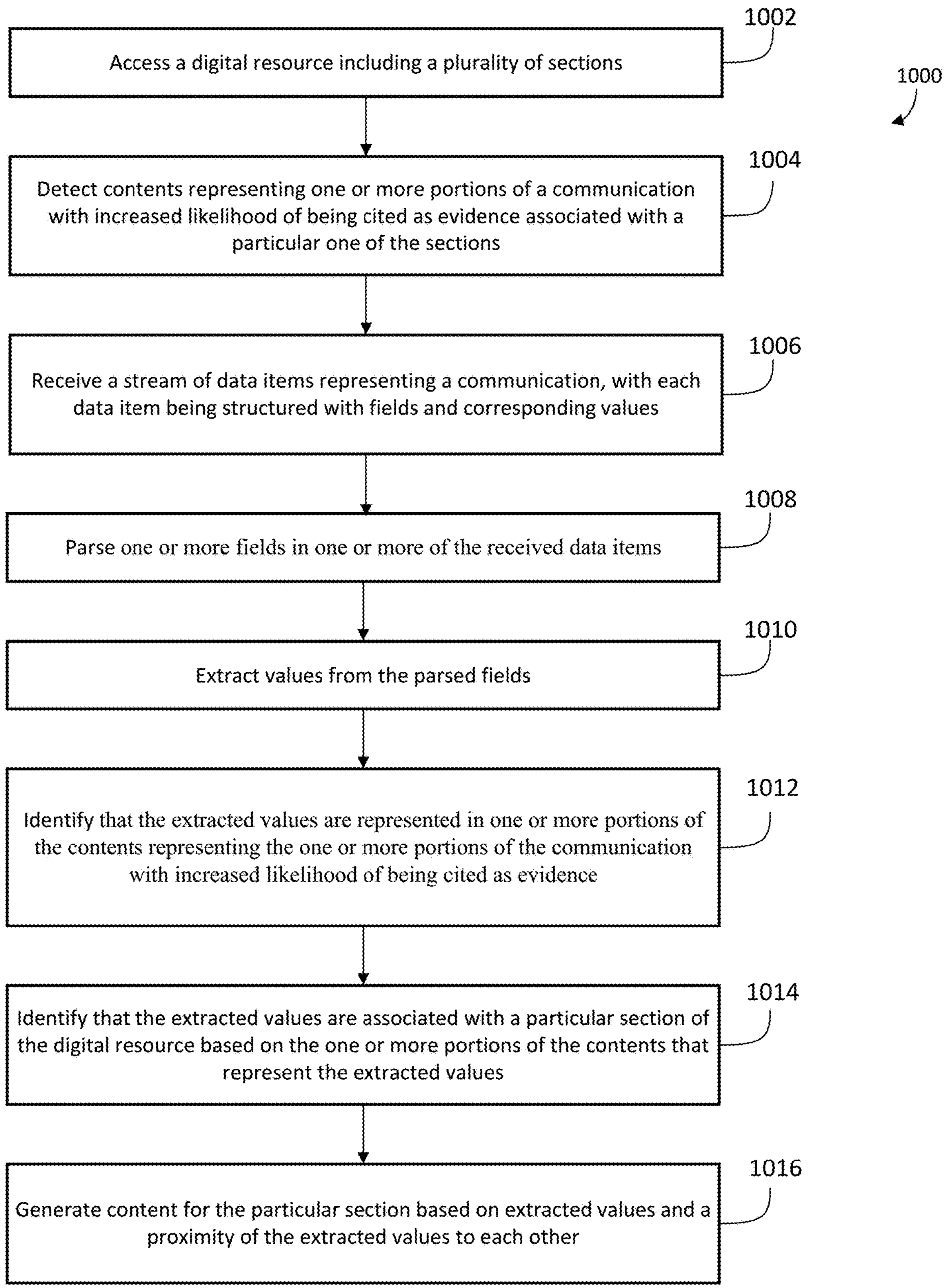
FIG. 10 is a flowchart of an exemplary process, consistent with disclosed embodiments.

FIG. 10 shows a flowchart representing a process 1000 for automatic generation, by a data processing system, of formatted annotations of conversations, such as conversations between patients and doctors. The process 1000 includes accessing (1002) a digital resource that includes a plurality of sections. The process 1000 includes accessing (1004), from a hardware storage device, a classifier configured to detect contents representing one or more portions of a communication with increased likelihood of being cited as evidence associated with a particular one of the sections, relative to a likelihood of one or more portions of another communication being cited as the evidence. The process 1000 includes receiving (1006), from one or more data sources, a stream of data items representing a communication, with each data item being structured with fields and corresponding values. The process 1000 includes generating content for at least one of the sections by performing the following operations. The operations include parsing (1008), by the data processing system, one or more fields in one or more of the received data items. The operations include extracting (1010), by the data processing system, values from the one or more parsed fields. The operations include identifying (1012), by the classifier, that the extracted values are represented in one or more portions of the contents representing the one or more portions of the communication with increased likelihood of being cited as evidence. The operations include, based on the one or more portions of the contents that represent the extracted values, identifying (1014) that the extracted values are associated with a particular section of the digital resource. The operations include, based on the extracted values and a proximity of the extracted values to each other in the one or more of the received data items, generating (1016) content for that particular section.

Figure 11:
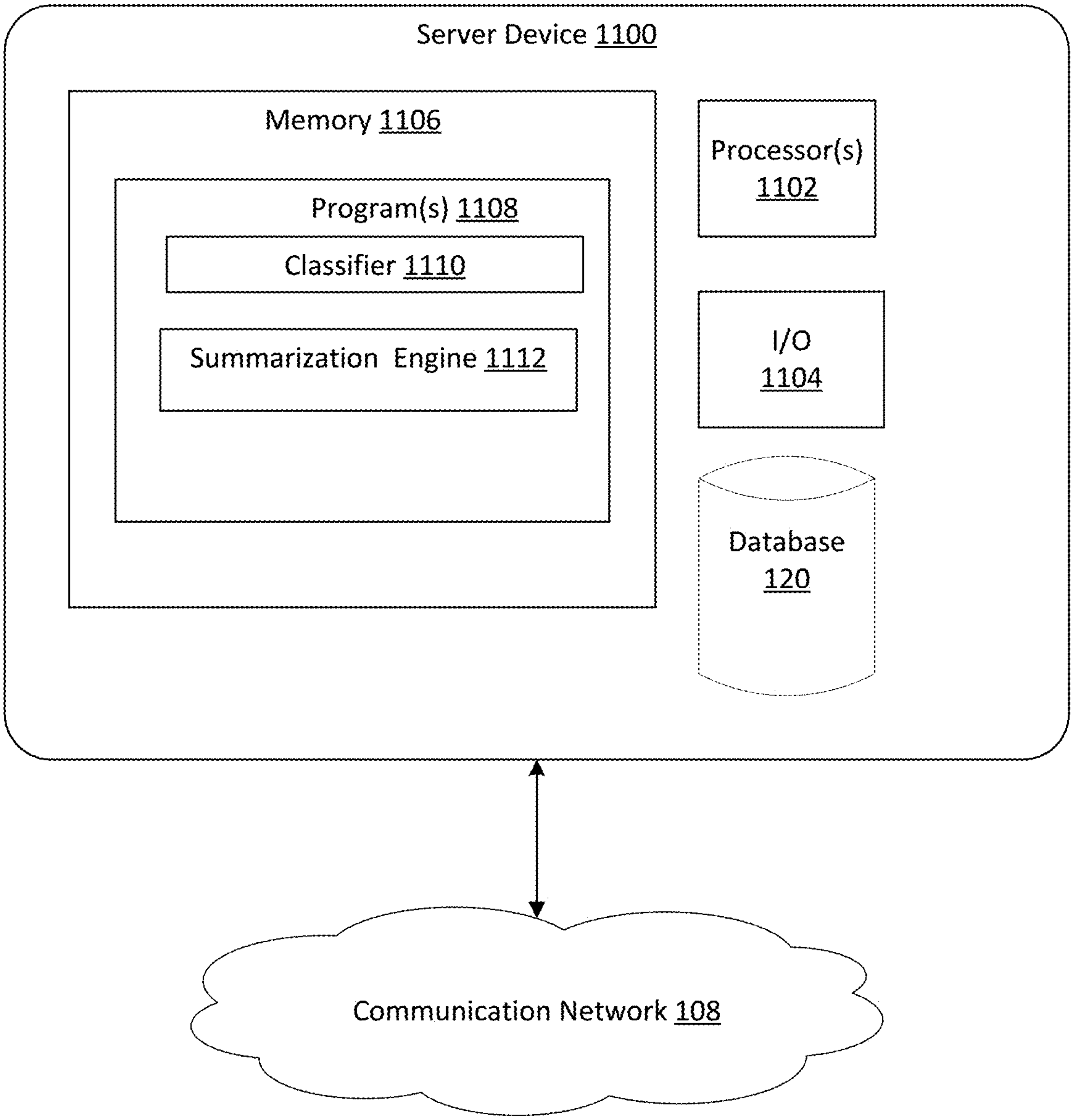
FIG. 11 is a block diagram of an exemplary server, consistent with disclosed embodiments.

FIG. 11 shows an exemplary server 1100 consistent with the disclosed embodiments. Variations of exemplary server 1100 may constitute one or more components of data processing system 110. In one embodiment, server 1100 includes one or more processors 1102, one or more input/output (I/O) devices 1104, and one or more memories 1106. In some embodiments, server 1100 may be a part of data processing system 110. In some embodiments, server 1100 may take the form of a specially programmed server or computing system used by data processing system 110. In some embodiments, server 1100 may be configured as an apparatus, embedded system, dedicated circuit, and the like based on the storage, execution, and/or implementation of the software instructions that perform one or more operations consistent with the disclosed embodiments. Processor 1102 may include one or more known processing devices, such as a microprocessor from the Pentium™ or Xeon™ family manufactured by Intel™, or the Turion™ family manufactured by AMD™, for example. The disclosed embodiments are not limited to any type of processor(s) otherwise configured to meet the computing demands required of different components of system 100.

Memory 1106 may include one or more storage devices configured to store instructions used by processor 1102 to perform functions related to described embodiments. For example, memory 1106 may be configured with one or more software instructions, such as program(s) 1108 that may perform one or more operations when executed by processor 1102. The disclosed embodiments are not limited to separate programs or computers configured to perform dedicated tasks. For example, memory 1106 may include a single program 308 that performs the functions of system 100, or program 1108 may comprise multiple programs. In certain embodiments, memory 1106 may store sets of instructions or programs 1108 for generating automated SOAP notes. These sets of instructions may be executed by processor 1102 to perform communication and/or processes consistent with disclosed embodiments. In certain embodiments, when server 1100 constitutes one or more of the components of data processing system 110, memory 1106 includes a classifier 1110 and a summarization engine 1112 similar to classifier 114 and summarization engine 116 as disclosed in FIG. 1.

Server 1100 may also be communicatively coupled to one or more database(s) 120. In one aspect, server 1100 may include database 120. Alternatively, database 120 may be located remotely from server 1100 and server 1100 may be communicatively coupled to database(s) 120 through network 108.

While the previous discussion is related to automated generation formatted annotations, discussion of these processes and environments are made by example only. It should be appreciated, however, that the present disclosure is not limited to these specific embodiments and details, which are exemplary only. It is further understood that one possessing ordinary skill in the art, in light of known systems and methods, would appreciate the use of the embodiments of the present disclosure for their intended purposes and benefits in any number of alternative embodiments, depending on specific design and other needs.

What is claimed is:

1. A method implemented by a data processing system, including:

accessing a digital resource that includes a plurality of sections;

accessing, from a hardware storage device, a hierarchical classifier configured to detect one or more portions of a communication with increased likelihood of being cited as evidence associated with a particular one of the sections, relative to a likelihood of one or more portions of another communication being cited as the evidence for the particular one of the sections;

receiving, from one or more data sources, a stream of data representing a communication;

for each section of the plurality of sections:

extracting, from the stream of data by a first portion of the hierarchical classifier, utterances from the communication by:

identifying a diagnosis or symptom relevant to the section as defined in a medical-entity-matching baseline;

identifying, based on section embedding data associated with the section, a portion of the communication previously used as evidence for one or more natural language summaries; or identifying, based on section embedding data associated with the section, a portion of the communication associated with a ground truth label of the hierarchical classifier;

clustering an utterance that is extracted from the communication with similar utterances into a cluster when a proximity of the utterance is less than a threshold distance in the communication from the similar utterances, the threshold distance tuned to cause a first number of clusters for the communication to approximate a second number of clusters in ground truth data, wherein each cluster forms a sentence in a natural language summary of content of the cluster;

repeating the clustering until the communication is divided into a set of proximity-based clusters including the cluster, sorting the cluster among the clusters of the section, the sorting based on an earliest respective utterance in each of the clusters;

for each sorted cluster of the section, applying a second portion of the hierarchical classifier to utterances of the cluster, the second portion of the hierarchical classifier including a multi-label classifier that generates an output representing an increased likelihood of each utterance of the cluster being cited as evidence for the section in the natural language summary of the communication, the multi-label classifier being conditioned based on the section that is selected each utterance input to the multi-label classifier being contextualized with other utterances of the cluster;

based on applying the multi-label classifier to the utterances in the cluster, generating a natural language summary of content in the cluster; and repeating application of the multi-label classifier to each of the proximity-based clusters for the section to generate the natural language summary of the section; and combining the natural language summary for each section into a structured record.

2. The method of claim 1, wherein the natural language summary of the content generated for the section is generated in response to identifying, by the hierarchical classifier, a diagnosis or symptom associated with the extracted utterances.

3. The method of claim 1, further comprising:

receiving metadata values associated with the extracted utterances, the metadata values representing one or more of a speaker identity or a temporal position in the stream of data representing the communication; and generating the natural language summary of the content for the section based on the metadata values associated with the extracted utterances.

4. The method of claim 1, wherein the sections include a subjective section comprising data representing at least one of patient behavior of a patient, patient complaint, symptoms, progress from last encounter, problem, medical issues impacting or influencing patient's day-to-day routine, family history, medical history, and a social history communicated in the communication;

wherein the sections include an objective section including data representing quantifiable data in the communication;

wherein the sections include an assessment section including data representing at least one of a physician diagnoses; and wherein the sections include a plan section representing plans for future care of the patient.

5. The method of claim 1, further comprising:

receiving training data representing labeled portions of communications with increased likelihood of being cited as evidence associated with a given section;

training the hierarchical classifier using the training data; and identifying, by the hierarchical classifier, based on the training, that the extracted utterances are represented in the stream of data representing the one or more portions of the communication with increased likelihood of being cited as evidence.

6. The method of claim 1, further comprising:

obtaining audio data representing the communication; and generating, using natural language processing (NLP), the stream of data representing the communication, the stream of data comprises a transcript of the communication.

7. The method of claim 1, further comprising:

merging two or more extracted utterances into a merged utterance, wherein generating the natural language summary of the content for the section is based on the merged utterance.

8. The method of claim 1, further comprising:

determining that the extracted utterances have been previously classified as representing one or more portions of a given communication with increased likelihood of being cited as evidence.

9. The method of claim 1, further comprising:

generating a structured entry for a data store, the structured entry including the generated natural language summary of the content for the section; and sending the structured entry to the data store for storage of the structured entry.

10. The method of claim 1, further comprising:

based on the section associated with each of the utterances of the communication, generating inferred information that his not mentioned in the communication, the inferred information including a disease prediction for a patient or a prediction of a medical history of a patient.

11. A data processing system, including:

at least one processing device; and a memory storing instructions that, when executed by the at least one processing device, cause the at least one processing device to perform operations including:

accessing a digital resource that includes a plurality of sections;

accessing, from a hardware storage device, a hierarchical classifier configured to detect one or more portions of a communication with increased likelihood of being cited as evidence associated with a particular one of the sections, relative to a likelihood of one or more portions of another communication being cited as the evidence for the particular one of the sections;

receiving, from one or more data sources, a stream of data representing a communication;

for each section of the plurality of sections:

extracting, from the stream of data by a first portion of the hierarchical classifier, utterances from the communication by:

identifying a diagnosis or symptom relevant to the section as defined in a medical-entity-matching baseline;

identifying, based on section embedding data associated with the section, a portion of the communication previously used as evidence for one or more natural language summaries; or identifying, based on section embedding data associated with the section, a portion of the communication associated with a ground truth label of the hierarchical classifier;

clustering an utterance that is extracted from the communication with similar utterances into a cluster when a proximity of the utterance is less than a threshold distance in the communication from the similar utterances, the threshold distance tuned to cause a first number of clusters for the communication to approximate a second number of clusters in ground truth data, wherein each cluster forms a sentence in a natural language summary of content of the cluster;

repeating the clustering until the communication is divided into a set of proximity-based clusters including the cluster, sorting the cluster among the clusters of the section, the sorting based on an earliest respective utterance in each of the clusters;

for each sorted cluster of the section, applying a second portion of the hierarchical classifier to utterances of the cluster, the second portion of the hierarchical classifier including a multi-label classifier that generates an output representing an increased likelihood of each utterance of the cluster being cited as evidence for the section in the natural language summary of the communication, the multi-label classifier being conditioned based on the section that is selected each utterance input to the multi-label classifier being contextualized with other utterances of the cluster;

based on applying the multi-label classifier to the utterances in the cluster, generating a natural language summary of content in the cluster; and repeating application of the multi-label classifier to each of the proximity-based clusters for the section to generate the natural language summary of the section; and combining the natural language summary for each section into a structured record.

12. The data processing system of claim 11, wherein the natural language summary of the content generated for the section is generated in response to identifying, by the hierarchical classifier, a diagnosis or symptom associated with the extracted utterances.

13. The data processing system of claim 11, the operations further including:

receiving metadata values associated with the extracted utterances, the metadata values representing one or more of a speaker identity or a temporal position in the stream of data representing the communication; and generating the natural language summary of the content for the section based on the metadata values associated with the extracted utterances.

14. The data processing system of claim 11, wherein the sections include a subjective section comprising data representing at least one of patient behavior of a patient, patient complaint, symptoms, progress from last encounter, problem, medical issues impacting or influencing patient's day-to-day routine, family history, medical history, and a social history communicated in the communication;

wherein the sections include an objective section including data representing quantifiable data in the communication;

wherein the sections include an assessment section including data representing at least one of a physician diagnoses; and wherein the sections include a plan section representing plans for future care of the patient.

15. The data processing system of claim 11, the operations further including:

receiving training data representing labeled portions of communications with increased likelihood of being cited as evidence associated with a given section;

training the hierarchical classifier using the training data; and identifying, by the hierarchical classifier, based on the training, that the extracted values are represented in the stream of data representing the one or more portions of the communication with increased likelihood of being cited as evidence.

16. The data processing system of claim 11, the operations further including:

obtaining audio data representing the communication; and generating, using natural language processing (NLP), the stream of data representing the communication, the stream of data comprises a transcript of the communication.

17. The data processing system of claim 11, the operations further including:

merging two or more extracted values into a merged value representing the two or more values, wherein generating the natural language summary of the content for the section is based on the merged value.

18. The data processing system of claim 11, further comprising:

determining that the extracted utterances have been previously classified as representing one or more portions of a given communication with increased likelihood of being cited as evidence.

19. The data processing system of claim 11, the operations further including:

generating a structured entry for a data store, the structured entry including the generated natural language summary of the content for the section; and sending the structured entry to the data store for storage of the structured entry.

20. One or more non-transitory computer-readable media storing instructions that, when executed by at least one processing device, cause the at least one processing device to perform operations including:

accessing a digital resource that includes a plurality of sections;

accessing, from a hardware storage device, a hierarchical classifier configured to detect one or more portions of a communication with increased likelihood of being cited as evidence associated with a particular one of the sections, relative to a likelihood of one or more portions of another communication being cited as the evidence for the particular one of the sections;

receiving, from one or more data sources, a stream of data representing a communication;

for each section of the plurality of sections:

extracting, from the stream of data by a first portion of the hierarchical classifier, utterances from the communication by:

identifying a diagnosis or symptom relevant to the section as defined in a medical-entity-matching baseline;

identifying, based on section embedding data associated with the section, a portion of the communication previously used as evidence for one or more natural language summaries; or identifying, based on section embedding data associated with the section, a portion of the communication associated with a ground truth label of the hierarchical classifier;

clustering an utterance that is extracted from the communication with similar utterances into a cluster when a proximity of the utterance is less than a threshold distance in the communication from the similar utterances, the threshold distance tuned based on ground truth data to cause a first number of clusters for the communication to approximate a second number of clusters in the ground truth data, wherein each cluster forms a sentence in a natural language summary of content of the cluster;

repeating the clustering until the communication is divided into a set of proximity-based clusters including the cluster, sorting the cluster among the clusters of the section, the sorting based on an earliest respective utterance in each of the clusters;

for each sorted cluster of the section, applying a second portion of the hierarchical classifier to utterances of the cluster, the second portion of the hierarchical classifier including a multi-label classifier that generates an output representing an increased likelihood of each utterance of the cluster being cited as evidence for the section in the natural language summary of the communication, the multi-label classifier being conditioned based on the section that is selected each utterance input to the multi-label classifier being contextualized with other utterances of the cluster;

based on applying the multi-label classifier to the utterances in the cluster, generating a natural language summary of content in the cluster; and repeating application of the multi-label classifier to each of the proximity-based clusters for the section to generate the natural language summary of the section; and combining the natural language summary for each section into a structured record.

21. The one or more non-transitory computer-readable media of claim 20, wherein the natural language summary of the content generated for the section is generated in response to identifying, by the classifier, a diagnosis or symptom associated with the extracted utterances.

22. The one or more non-transitory computer-readable media of claim 20, the operations further including:

receiving metadata values associated with the extracted utterances, the metadata values representing one or more of a speaker identity or a temporal position in the stream of data representing the communication; and generating the natural language summary of the content for the section based on the metadata values associated with the extracted utterances.

23. The one or more non-transitory computer-readable media of claim 20, wherein the sections include a subjective section comprising data representing at least one of patient behavior of a patient, patient complaint, symptoms, progress from last encounter, problem, medical issues impacting or influencing patient's day-to-day routine, family history, medical history, and a social history communicated in the communication;

wherein the sections include an objective section including data representing quantifiable data in the communication;

wherein the sections include an assessment section including data representing at least one of a physician diagnoses; and wherein the sections include a plan section representing plans for future care of the patient.

24. The one or more non-transitory computer-readable media of claim 20, the operations further including:

receiving training data representing labeled portions of communications with increased likelihood of being cited as evidence associated with a given section;

training the classifier using the training data; and identifying, by the classifier, based on the training, that the extracted utterances are represented in the stream of data representing the one or more portions of the communication with increased likelihood of being cited as evidence.

25. The one or more non-transitory computer-readable media of claim 20, the operations further including:

obtaining audio data representing the communication; and generating, using natural language processing (NLP), the stream of data representing the communication, the stream of data comprises a transcript of the communication.

26. The one or more non-transitory computer-readable media of claim 20, the operations further including:

merging two or more extracted utterances into a merged utterance, wherein generating the natural language summary of the content for the section is based on the merged utterance.

27. The one or more non-transitory computer-readable media of claim 20, the operations further including:

generating a structured entry for a data store, the structured entry including the generated natural language summary of the content for the section; and sending the structured entry to the data store for storage of the structured entry.

* * * * *